(12) United States Patent
Mahadevan-Jansen et al.

(10) Patent No.: US 7,508,524 B2
(45) Date of Patent: Mar. 24, 2009

(54) COMBINED RAMAN SPECTROSCOPY-OPTICAL COHERENCE TOMOGRAPHY (RS-OCT) SYSTEM AND APPLICATIONS OF THE SAME

(75) Inventors: Anita Mahadevan-Jansen, Nashville, TN (US); Ton Van Leeuwen, Bussum (NL); Chetan A. Patil, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 11/780,793

(22) Filed: Jul. 20, 2007

(65) Prior Publication Data

US 2009/0021724 A1 Jan. 22, 2009

(51) Int. Cl.
*G01B 9/02* (2006.01)
(52) U.S. Cl. .......................... 356/479; 356/73; 356/301
(58) Field of Classification Search ................. 356/456, 356/479, 484, 451, 73; 250/339.07, 339.08
See application file for complete search history.

(56) References Cited

U.S. PATENT DOCUMENTS

| | | | | |
|---|---|---|---|---|
| 6,002,480 | A * | 12/1999 | Izatt et al. | 356/479 |
| 7,075,658 | B2 * | 7/2006 | Izatt et al. | 356/479 |
| 2003/0218756 | A1 * | 11/2003 | Chen et al. | 356/497 |
| 2004/0260183 | A1 * | 12/2004 | Lambert et al. | 600/476 |
| 2005/0283058 | A1 * | 12/2005 | Choo-Smith et al. | 600/315 |
| 2006/0066865 | A1 * | 3/2006 | Tsujita | 356/479 |
| 2006/0142746 | A1 * | 6/2006 | Friedman et al. | 606/11 |
| 2007/0088219 | A1 * | 4/2007 | Xie et al. | 600/473 |

OTHER PUBLICATIONS

Cancer Reference Information: Skin Cancer, American Cancer Society. 2006.
Haka, A.S., et al., In vivo *margin assessment during partial mastectomy breast surgery using raman spectroscopy*. Cancer Res, 2006. 66(6): p. 3317-3322.
Haka, A.S., et al., *Identifying microcalcifications in benign and malignant breast lesions by probing differences in their chemical composition using Raman spectroscopy*. Cancer Res, 2002. 62(18): p. 5375-5380.

(Continued)

*Primary Examiner*—Tarifur Chowdhury
*Assistant Examiner*—Jonathan M Hansen
(74) *Attorney, Agent, or Firm*—Morris, Manning & Martin LLP; Tim Tingkang Xia

(57) ABSTRACT

An apparatus for evaluating a target of interest of a living subject. In one embodiment, the apparatus has a first light source for generating a broadband light, a second light source for generating a monochromatic light, a beamsplitter optically coupled to the first light source for receiving the broadband light and splitting it into a reference light and a sample light, a reference arm optically coupled to the beamsplitter for receiving the reference light and returning it into the beamsplitter, and a probe having a working end placed proximal to a target of interest of a living subject, optically coupled to the beamsplitter and the second light source for receiving the sample light and the monochromatic light, delivering them from the working end to the target of interest, collecting from the working end a backscattering light and a Raman scattering light that are obtained from interaction of the sample light and the monochromatic light with the target of interest, respectively, and returning the backscattering light into the beamsplitter so as to generate an interference signal between the returned backscattering light and the returned reference light in the beamsplitter.

57 Claims, 13 Drawing Sheets

OTHER PUBLICATIONS

Frank, C.J., R.L. McCreery, and D.C. Redd, *Raman spectroscopy of normal and diseased human breast tissues*. Anal Chem, 1995. 67(5): p. 777-783.

Stone, N., et al., *Raman spectroscopy for identification of epithelial cancers*. Faraday Discuss, 2004. 126: p. 141-157; discussion 169-83.

Crow, P., et al., *Assessment of fiberoptic near-infrared raman spectroscopy for diagnosis of bladder and prostate cancer*. Urology, 2005. 65(6): p. 1126-1130.

Huang, Z., et al., *Near-infrared Raman spectroscopy for optical diagnosis of lung cancer*. Int J Cancer, 2003 107(6): p. 1047-1052.

Molckovsky, A., et al., *Diagnostic potential of near-infared Raman spectroscopy in the colon: differentiating adenomatous from hyperplastic polyps*. Gastrointest Endosc, 2003. 57(3): p. 396-402.

Huang, D. et al., *Optical Coherence Tomography*. Science, 1991. 254(5035): p. 1178-1181.

Izatt, J.A., et al., In vivo *bidirectional color Doppler flow imaging of picoliter blood volumes using optical coherence tomography*. Optics Letters, 1997. 22(18): p. 1439-1441.

deBoer, J.F., et al., *Two-dimensional birefringence imaging in biological tissue by polarization-sensitive optical coherence tomography*. Optics Letters, 1997. 22(12): p. 934-936.

Morgner, U., et al., *Spectroscopic optical coherence tomography*. Optics Letters, 25(2): p. 111-113.

Faber, D.J., et al., *Light absorption of (oxy-)hemoglobin assessed by spectroscopic optical coherence tomography*. Opt Lett, 2003. 28(16): p. 1436-1438.

Thomas, D. and G. Duguid, *Optical coherence tomography—a review of the principles and contemporary uses in retinal investigation*. Eye, 2004. 18(6):561-570.

Hee, M.R., et al., *Optical Coherence Tomography of the Human Retina*. Archives of Ophthalmology, 1995. 113(3): p. 325-332.

Chalita, M.R., et al., *High-speed optical coherence tomography of laser iridotomy*. Am J Opthalmol, 2005. 140(6): p. 1133-1136.

Swanson, E.A., et al., In-Vivo *Retinal Imaging by Optical Coherence Tomography*. Optics Letters, 1993. 18(21): p. 1864-1866.

Sivak, M.V., Jr., et al., *High-resolution endoscopic imaging of the GI tract using optical coherence tomography*. Gastrointest Endosc, 2000. 51(4 Pt 1): p. 474-479.

Jang, I.K., G. Tearney, and B. Bouma, *Visualization of tissue prolapse between coronary stent struts by optical coherence tomography: comparison with intravascular ultrasound*. Circulation, 2001. 104(22): p. 2754.

Welzel, J., *Optical coherence tomography in dermatology: a review*. Skin Res Technol, 2001. 7(1): p. 1-9.

Vargas, G., et al., *Use of an agent to reduce scattering in skin*. Lasers Surg Med, 1999. 24(2): p. 133-141.

Welzel, J., M. Bruhns, and H.H. Wolff, *Optical coherence tomography in contact dermatitis and psoriasis*. Arch Dermatol Res, 2003. 295(2): p. 50-55.

Welzel, J., et al., *Changes in function and morphology of normal human skin: evaluation using optical coherence tomography*. Br J Dermatol, 2004. 150(2): p. 220-225.

Park, B.H., et al., In vivo *burn depth determination by high-speed fiber-based polarization sensitive optical coherence tomography*. J Biomed Opt, 2001. 6(4): p. 474-479.

Pierce, M.C., et al., *Collagen denaturation can be quantified in burned human skin using polarization-sensitive optical coherence tomography*. Burns, 2004. 30(6): p. 511-517.

Srinivas, S.M., et al., *Determination of burn depth by polarization-sensitive optical coherence tomography*. J Biomed Opt, 2004. 9(1): p. 207-212.

Bechara, F.G., et al., *Histomorphologic correlation with routine histology and optical coherence tomography*. Skin Res Technol, 2004. 10(3): p. 169-173.

de Giorgi, V., et al., *Possible histopathologic correlates of dermoscopic features in pigmented melanocytic lesions identified by means of optical coherence tomography*. Exp Dermatol, 2005. 14(1): p. 56-59.

Rollins, A.M., et al., In vivo *video rate optical coherence tomography*. Optics Express, 1998. 3(6): p. 219-229.

Mahadevan-Jansen, A. and R. Richards-Kortum, *Raman Spectrscopy for the Detection of Cancers and Precancers*. Journal of Biomedical Optics, 1996. 1(1): p. 31-70.

\* cited by examiner

COMBINED RAMAN SPECTROSCOPY-OPTICAL COHERENCE TOMOGRAPHY (RS-OCT) SYSTEM AND APPLICATIONS OF THE SAME

CROSS-REFERENCE TO RELATED PATENT APPLICATION

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [9] represents the 9th reference cited in the reference list, namely, Mahadevan-Jansen, A., et al., Near-infrared Raman spectroscopy for in vitro detection of cervical precancers. Photochem Photobiol, 1998. 68(1): p. 123-132.

FIELD OF THE INVENTION

The present invention generally relates to a system for non-invasive diagnosis of normal and cancerous skin lesions of a living subject, and in particular to a system that integrates Raman spectroscopy (RS) with optical coherence tomography (OCT), for non-invasive evaluation of the biochemical compositions and morphological details of normal and cancerous skin lesions of a living subject and applications of the same.

BACKGROUND OF THE INVENTION

Skin cancer is the most commonly occurring of all cancers, accounting for more than a million incidences in the United States annually [1]. There are three types of skin cancer including basal cell carcinoma (BCC) and squamous cell carcinoma (SCC), and malignant melanoma.

BCC arises from transformed epidermal stem cells in the basal layer of the epidermis, such that upon pathological analysis, tumor cells have a characteristically columnar appearance. BCC tends to form nests of the tumor cells whose peripheral borders appear as an orderly line of basal cells (termed "peripheral pallisading") and whose centers possess similar cell types with low amounts of cytoplasm. Clinically, BCC presents in four variants: superficial, nodular, pigmented, and sclerosing [2]. Clinical recognition of the BCC variants can be difficult because of their resemblance to other clinical entries such as sebaceous hyperplasia and molluscum contagiosum (nodular BCC) or eczema and psoriasis (superficial BCC).

SCC originates from transformed cells in the stratum spinosum, and has the potential to develop downwards and invade into underlying structures. SCC appears pathologically different from BCC. The tumor nests in SCC are bordered by polygonal cells with larger degrees of cytoplasm than that in BCC. SCC tumor cells also differentiate towards the center of the nests such that the nest centers often have sections of keratinized epidermal cells which appear as "keratinized pearls" [3]. Clinical differentiation of SCC from other skin lesions also normally requires histo-pathological analysis as they can often be confused with keratoacanthomas.

Melanomas arise from transformed melanocytes in the basal layer of the epidermis. The cancerous cells then spread upwards into the epidermis as well as downwards into the dermis and underlying tissues. Clinically, melanomas appear as dark pigmented lesions with four subtypes: Lentigo maligna, superficial spreading melanoma, acral lentiginous melanoma, and nodular melanoma. The first three melanomas initially spread horizontally for years before vertical invasion, and therefore have an excellent prognosis if diagnosed early enough. Nodular melanoma, however, almost immediately begins a vertical growth phase and is therefore associated with a much worse prognosis.

Currently, the gold standard for skin cancer diagnosis is histopathological evaluation of tissue biopsies. Depending on the nature of the skin lesion, different types of biopsies are performed. For protruded skin lesions believed not to be melanocytic, a shave biopsy is performed. For flat lesions and lesions where it is imperative that a full-thickness specimen is taken, a punch biopsy may be advantageous. Almost all small lesions suspected to be melanocytic, however, are removed via excisional biopsy. The excisional biopsy removes the entire lesion including a margin of normal skin at a depth that extends into the subcutaneous tissue. This is to ensure proper analysis of the depth profile of the lesion as well as a precautionary method. In suspicious lesions that are potentially non-melanomas, incisional biopsies are taken where only a portion of the lesion is removed for histological analysis.

Although the current gold standard for evaluation of potentially cancerous skin lesions is effective, it is far from perfect. Biopsy is an invasive and painful procedure that is often unnecessary when the lesions are benign. The biopsy is also a time-consuming and expensive procedure. Additionally, in patients who present with multiple similarly appearing lesions, the selection of the site for biopsy is subjective and could result in misdiagnosis [2]. Thus, there remains a need for a non-invasive technique that can reliably analyze suspicious lesions in situ in real-time and serve as a method to initially guide biopsy and eventually potentially serve as a replacement for histo-pathological analysis.

Raman spectroscopy (RS) is an optical technique that probes the specific molecular content of a sample by collecting in-elastically scattered light. Raman spectroscopy is a regularly used tool in analytical chemistry to determine the presence of specific molecules in mixed samples. Recent studies have shown RS can be utilized for investigating cancerous human tissues. Examples include the analysis of tissues from the breast [4-7], cervix [8,9], bladder and prostate [10], lung [11], and GI tract [12]. Although Raman spectroscopy has been proven to be a powerful tool for the biochemical analysis of tissue, a significant limitation lies in its inability to practically relate biochemical data to tissue structure.

Optical coherence tomography (OCT) is a recently developed imaging modality capable of generating cross-sectional images of tissue micro-structure [13], function [14], and optical properties [15-17]. Clinical applications include imaging of the retina [18] and anterior chamber of the eye [19-22], GI tract [23], coronary vasculature [24]. OCT has also been applied to the in vivo imaging of the skin to examine dermatitis, psoriasis, as well as the effect of varies ointments, water, tape stripping, and UV radiation on normal skin [25-29]. Additionally, the polarization-sensitive OCT has been employed to assess burn depth based on changes in dermal collagen structure [30-32]. Applications of OCT for the imaging of skin cancers, however, have been limited. Initial studies have demonstrated OCT's ability to image tumor nests in basal cell carcinomas, as well as the structure of the horny cysts in seborrheic keratosis [25]. Additional studies have shown the appearance of melanocytic nevi and their correlation with histopathology [33, 34]. However, while OCT is capable of producing cross-sectional images of tissue microstructure with near histological resolution, conventional application prohibits determination of the biochemical composition of tissue anomalies and defects.

Therefore, a heretofore unaddressed need exists in the art to address the aforementioned deficiencies and inadequacies.

SUMMARY OF THE INVENTION

In one aspect, the present invention relates to an apparatus that uses Raman spectroscopy and optical coherence tomography for non-invasively evaluating a target of interest of a living subject. The target of interest in one embodiment includes tissues of the living subject.

In one embodiment, the apparatus includes a first light source for generating a broadband light and a second light source for generating a monochromatic light at a single wavelength, $\lambda 2$, which is in the range of 600-1000 nm. The broadband light is characterized with a center wavelength, $\lambda 1$, which is in the range of 1100-1500 nm, and a spectral bandwidth, $\Delta$, which is in the range of 20-100 nm. In one embodiment, the first light source includes light emitting diodes (LEDs), femtosecond lasers, broadband optical amplifiers, or the like. The second light source comprises a laser.

The apparatus further includes a beamsplitter optically coupled to the first light source for receiving the broadband light and splitting the received broadband light into a reference light and a sample light.

The apparatus also includes a reference arm optically coupled to the beamsplitter for receiving the reference light and returning the received reference light into the beamsplitter. The reference arm is arranged such that the length of an optical path of the reference light propagating from the beamsplitter through the reference arm and back the beamsplitter is adjustable. In one embodiment, the reference arm has a mirror movable along the optical path of the reference light so as to adjust the optical path length. In another embodiment, the reference arm comprises a rapid scanning optical delay (RSOD) for adjusting the optical path length. The RSOD includes a fiber optical collimator, a grating, a phase control delay lens and a galvanometric mirror respectively placed along the optical path in such a configuration that in operation, the reference light is received by the fiber optical collimator and collimated onto the grating, and redirected by the grating to the galvanometric mirror through the phase control delay lens, which scans the reference light back towards the fiber optical collimator through the phase control delay lens and the grating, thereby adjusting the optical path length of the reference light propagating through the reference arm.

Furthermore, the apparatus includes a probe. The probe has a working end placed proximal to a target of interest of a living subject, and is optically coupled to the beamsplitter and the second light source for receiving the sample light and the monochromatic light, delivering them from the working end onto the target of interest, collecting from the working end a backscattering light and a Raman scattering light that are obtained from interaction of the sample light and the monochromatic light with the target of interest, respectively, and returning the backscattering light into the beamsplitter so as to generate an interference signal between the returned backscattering light and the returned reference light in the beamsplitter.

The probe includes a casing having a first end and an opposite, second end, a first, a second and a third optical ports, where the first and second optical ports are located at the first end of the casing and the third optical port is located at the second end of the casing such that the first and third optical ports define a first optical path therebetween and the second and third optical ports define a second optical path therebetween, respectively. Each of the first and second optical paths has a first portion and a second portion, where the second portions of the first and second optical paths are substantially overlapped and proximal to the third optical port.

The probe further includes a collimation lens, a coupling lens, an objective lens, a first, a second and a third mirrors, a dual-band pass filter, a notch filter, and a scanning member. In one embodiment, the second mirror is a custom dichroic mirror configured to selectively transmit the Raman scattering light and reflect away light that is not the Raman scattering light. The scanning member includes at least one of micro-electronic mirrors (MEMS), micro-optoelectrical mirrors (MOEMS), galvanometer devices, rotation motors, translational motors, and any combinations of them. The objective lens includes an achromatic doublet objective lens or a fused silica objective lens.

In one embodiment, the collimation lens, the dual-band pass filter, the first mirror are placed at the first portion of the first optical path. The coupling lens and the notch filter are placed at the first portion of the second optical path. The second and third mirrors, the scanning member and the objective lens are placed at the overlapped second portion of the first and second optical paths. For such a configuration, in operation, the sample light and the monochromatic light are received from the first port and collimated by the collimation lens, passed through the dual-band pass filter and reflected to the galvanometer by the first, second and third mirrors, which telecentrically scans them through the objective lens and the third optical port onto the target of interest, which, in response to illumination by the sample light and the monochromatic light, backscatters the sample light and the monochromatic light in the forms of backscattering light and Raman scattering light, respectively, which are collected through the third optical port by the objective lens, and reflected by the scanning member and the third mirror to the second mirror, from which the backscattering light is reflected by the second mirror and the first mirror to the dual-band pass filter, and passed through the dual-band pass filter and the collimation lens to the first optical port, while the Raman scattering light is transmitted through the second mirror to the notch filter and the coupling lens to the second optical port.

The probe may include a first optical connector optically coupled between the first optical ports and a single-mode fiber (SMF), and a second optical connector optically coupled between the second optical port and a multi-mode fiber (MMF), respectively. The probe may also include a lens tube adjustably placed between the third port and a position where the target of interest is to be placed in operation.

Moreover, the apparatus includes a first detecting device optically coupled to the beamsplitter for collecting the interference signal to provide an interference pattern of the returned backscattering light and the returned reference light, and a second detecting device optically coupled to the probe for collecting the Raman scattering light to provide a frequency spectrum of the returned Raman scattering light. The interference pattern contains information of morphological details of the target of interest, while the frequency spectrum contains information of biochemical contents of the target of interest. The interference pattern of the interference signal is associated with an optical coherence tomographic (OCT) image. The spectral profile of the frequency spectrum of the Raman scattering light includes a plurality of intensity peaks at a plurality of wavelengths, each intensity peak associating with a specific biochemical content of the target of interest.

In one embodiment, the first detecting device has an OCT detector optically coupled to the beamsplitter and the optical circulator for receiving the OCT signal, a BP filter in communication with the OCT detector and a data acquisition (DAQ) member in communication with the BP filter. The second detecting device includes a spectrograph optically coupled to the probe for receiving the Raman scattering light, a charge-coupled detecting (CCD) camera in communication with the spectrograph and a DAQ member in communication with the CCD camera.

Additionally, the apparatus includes an optical circulator having three ports optically coupled to the first light source, the beamsplitter and the first detecting device, respectively. The optical circulator is configured such that when an optical signal is fed into and received by one of the three ports, the fed optical signal is transferred from the receiving port to a predetermined one of the other two ports port.

Furthermore, the apparatus includes a wavelength division multiplexer (WDM) optically coupled to the beamsplitter, the second light source and the probe for receiving the sample light and the monochromatic light from the beamsplitter and the second light source, respectively, and delivering the received sample and monochromatic light to the probe, and receiving the backscattering light from the probe and returning the received backscattering light into the beamsplitter.

The apparatus may include a controller in communication with the first and second detecting devices and programmed to correlate the OCT image with the Raman scattering spectrum and determine the structures and biochemical content of the target of interest from the correlated OCT image and Raman scattering spectrum. In one embodiment, the controller is a computer having a display for displaying the OCT image and the Raman scattering spectrum.

In another aspect, the present invention relates to an apparatus for non-invasively evaluating a target of interest of a living subject. In one embodiment, the apparatus has a first light source for generating a broadband light, a second light source for generating a monochromatic light, a beamsplitter optically coupled to the first light source for receiving the broadband light and splitting it into a reference light and a sample light, and a sample arm optically coupled to the beamsplitter and the second light source for combining the sample light and the monochromatic light, delivering the combined sample and monochromatic light to the target of interest, collecting a backscattering light and a Raman scattering light that are obtained from interaction of the sample light and the monochromatic light with the target of interest, respectively, and directing the collected backscattering light and Raman scattering light in different optical paths.

Additionally, the apparatus also has an OCT signal detector optically coupled to the beamsplitter for detecting the interference signal to provide an interference pattern of the returned backscattering light and the returned reference light, and a second detecting device optically coupled to the probe for detecting the Raman scattering light to provide a frequency spectrum of the returned Raman scattering light.

In one embodiment, the sample arm has (i) a first collimating lens optically coupled to the beamsplitter for receiving the sample light and collimating the received sample light into a first optical path; (ii) a second collimating lens optically coupled to the second light source for receiving the monochromatic light and collimating the received monochromatic light into a second optical path, wherein the first collimating lens (and the second collimating lens are substantially identical; (iii) a first dichroic mirror optically coupled to the first collimating lens and the second collimating lens for receiving the collimated sample light from the first collimating lens and the collimated monochromatic light from the second collimating lens and transmitting the received sample light into a third optical path and reflecting the received monochromatic light into the third optical path, respectively, such that the transmitted sample light and the reflected monochromatic light are combined in the third optical path; (iv) a second dichroic mirror optically coupled to the first dichroic mirror for receiving the combined sample and monochromatic light and reflecting it into a fourth optical path; (v) a scanning member optically coupled to the second dichroic mirror for receiving the reflected sample and monochromatic light and telecentrically scanning the received sample and monochromatic light onto a target of interest along a fifth optical path; and (vi) an objective lens optically coupled to the scanning member, placed at the fifth optical path and configured to receive the sample and monochromatic light scanned by the scanning member and focus the scanned sample and monochromatic light onto the target of interest. In response, the target of interest backscatters the sample light and the monochromatic light in the forms of a backscattering light and a Raman scattering light, respectively, which are collected and focused to the scanning member by the objective lens, and directed by the scanning member along the fourth optical path to the second dichroic mirror, from which the Raman scattering light is transmitted by the second dichroic mirror into a sixth optical path, while the backscattering light is reflected by the second dichroic mirror along the third optical to the first dichroic mirror, and transmitted by the first dichroic mirror along the first optical path to the first collimating lens.

The sample arm also has a dual-band pass filter placed at the second optical path between the second collimation lens and the first dichroic mirror, where the dual-band pass filter is characterized with a central bandpass wavelength corresponding to a wavelength of the monochromatic light.

The sample arm may have a coupling lens optically coupled to the second dichroic mirror and placed at the sixth optical path for receiving the Raman scattering light transmitted from the second dichroic mirror, and a notch filter placed at the sixth optical path between the second dichroic mirror and the coupling lens for eliminating residual elastically scattering light at the single wavelength of the monochromatic light.

In one embodiment, the beamsplitter includes an OCT 2×2 fiber coupler. The scanning member comprises at least one of MEMS, MOEMS, galvanometer devices, rotation motors, translational motors, and any combinations of them. The dichroic mirror is configured to reflect the monochromatic light and transmit a light that is not the monochromatic light. The dichroic mirror is configured to transmit the Raman scattering light and reflect a light that is not the Raman scattering light. The objective lens comprises an achromatic doublet objective lens or a fused silica objective lens.

The reference light transmits from the beamsplitter through the reference arm and returns into the beamsplitter along a reference path having a length that is adjustable. The sample light transmits from the beamsplitter through the sample arm to the target of interest, and is backscattered by the target of interest into the beamsplitter through the sample arm along a sample path having a length that is adjustable depending upon the structure of the target of interest to be examined.

In yet another aspect, the present invention relates to a method for non-invasively evaluating a target of interest of a living subject. In one embodiment, the method in the following steps: at first, a broadband light and a monochromatic light are generated. The broadband light is split into a reference light and a sample light. Then, the sample light and the monochromatic light are co-aligned into an optical path. The co-aligned sample and monochromatic light are scanned onto a target of interest along the optical path. Next, a backscattering light and a Raman scattering light that are obtained from interaction of the sample light and the monochromatic light with the target of interest, respectively, are collected. The collected backscattering light is interfered with the reference light to provide an interference signal. The interference signal and the Raman scattering light are processed to provide morphological details and biochemical contents of the target of interest, respectively.

In one embodiment, the interference signal is processed in the form of an optical coherence tomographic (OCT) image, and the Raman scattering light is processed in the form of a frequency spectrum having a plurality of intensity peaks at a plurality of wavelengths, each intensity peak associating with a specific biochemical content of the target of interest. The processing step comprises the step of correlating the OCT image with the frequency spectrum.

In a further aspect, the present invention relates to a probe usable in a combined Raman spectroscopy and optical coherence tomography (RS-OCT) system, having a casing having a first end and an opposite, second end. In one embodiment, the probe has a first, a second and a third optical ports, where the first and second optical ports are located at the first end of the casing and the third optical port is located at the second end of the casing such that the first and third optical ports define a first optical path therebetween and the second and third optical ports define a second optical path therebetween, respectively. Each of the first and second optical paths has a first portion and a second portion, where the second portions of the first and second optical paths are substantially overlapped and proximal to the third optical port.

The probe further has a collimation lens, a coupling lens, an objective lens, a first, a second and a third mirrors, and a scanning member for scanning a beam of light onto a target of interest of a living subject, wherein the beam of light comprises a broadband light and a monochromatic light. In one embodiment, the collimation lens and the first mirror are placed at the first portion of the first optical path. The coupling lens is placed at the first portion of the second optical path and proximal to the second optical port. The second and third mirrors, the galvanometer and the objective lens are placed at the overlapped second portion of the first and second optical paths.

For such an arrangement, in operation, the beam of light is received from the first port and collimated by the collimation lens onto the first mirror, and redirected to the scanning member by the first, second and third mirrors, which telecentrically scans the beam of light through the objective lens and the third optical port onto the target of interest, which, in response to illumination by the broadband light and the monochromatic light, backscatters the sample light and the monochromatic light in the forms of a backscattering light and a Raman scattering light, respectively, which are collected through the third optical port by the objective lens, and directed by the scanning member and the third mirror to the second mirror, from which the backscattering light is reflected by the second mirror and the first mirror onto the collimation lens and transmitted by the collimation lens to the first optical port, while the Raman scattering light is transmitted through the second mirror and the coupling lens to the second optical port.

Furthermore, the probe includes a first optical connector optically coupled between the first optical port and an SMF, and a second optical connector optically coupled between the second optical port and an MMF, respectively.

Moreover, the probe includes a dual-band pass filter placed at the first portion of the first optical path between the collimation lens and the first mirror, and adapted for filtering out fiber fluorescence, and a notch filter placed at the first portion of the second optical path between the coupling lens and the second mirror, and configured to eliminate a residual elastically scattering light backscattered from the target of interest. The probe may also have a lens tube adjustably placed between the third port and a position that the target of interest is to be placed in operation.

In one embodiment, the scanning member comprises at least one of MEMS, MOEMS, galvanometer devices, rotation motors, translational motors, or any combinations of them. The second mirror is a custom dichroic mirror configured to transmit the Raman scattering light and reflect a light that is not the Raman scattering light. The objective lens comprises an achromatic doublet objective lens or a fused silica objective lens.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
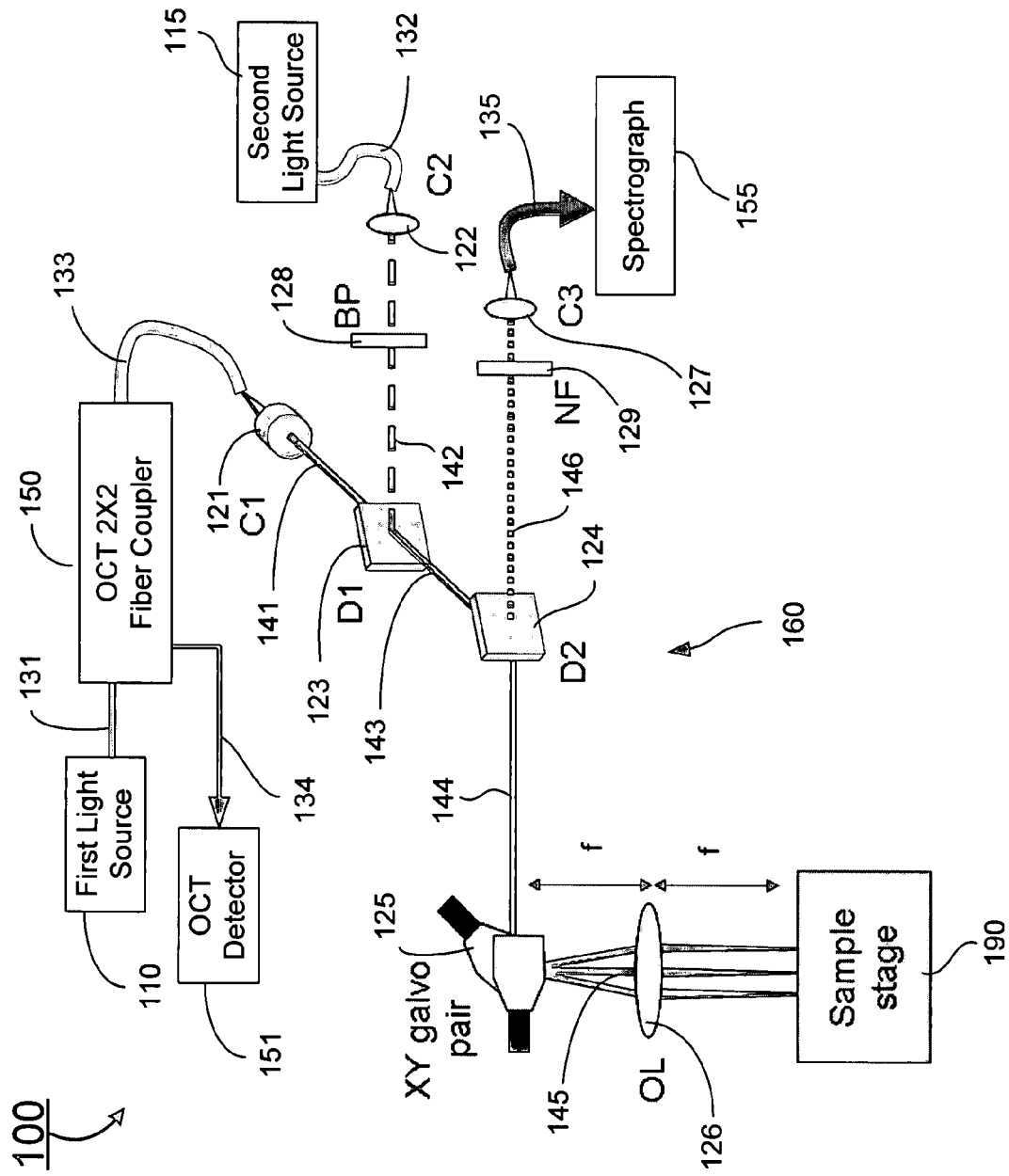
FIG. 1 shows a Raman spectroscopy-optical coherence tomography (RS-OCT) system according to one embodiment of the present invention. In this embodiment, both broadband light (OCT sample light) and Raman excitation light are collimated by two identical collimating lenses (C1, C2). A Band Pass filter (BP) is used to remove unwanted light from Raman excitation path. A dichroic mirror (D1) is utilized to ensure the OCT sample light and Raman excitation light to be co-aligned. A dichroic mirror (D2) is configured to redirect the OCT sample light and Raman excitation light to the target of interest while transmit Raman scattering light. A fused silica objective lens (OL) is utilized to focus and collect the backscattering light. A notch filter (NF) in the Raman collection path is employed to remove residual Raman excitation light before fiber coupling via a fused silica coupling lens (C3) into a multi-mode 100 µm fiber.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

As used herein, the term "living subject" refers to a human being such as a patient, or an animal such as a lab testing monkey.

As used herein, the term "Raman spectroscopy" refers to an optical technique that probes the specific molecular content of a sample by collecting in-elastically scattered light. As photons propagate through a medium, they undergo both absorptive and scattering events. In absorption, the energy of the photons is completely transferred to the material, allowing either heat transfer (internal conversion) or re-emission phenomena such as fluorescence and phosphorescence to occur. Scattering, however, is normally an in-elastic process, in which the incident photons retain their energy. In Raman scattering, the photons either donate or acquire energy from the medium, on a molecular level. In contrast to fluorescence, where the energy transfers are on the order of the electronic bandgaps, the energy transfers associated with Raman scattering are on the order of the vibrational modes of the molecule. These vibrational modes are molecularly specific, giving every molecule a unique Raman spectral signature.

Raman scattering is a very weak phenomena, and therefore practical measurement of Raman spectra of a medium requires high power excitation laser sources and extremely sensitive detection hardware. Even with these components, the Raman spectra from tissue are masked by the relatively intense tissue auto-fluorescence. After detection, post processing techniques are required to subtract the fluorescent background and enable accurate visualization of the Raman spectra. Raman spectra are plotted as a function of frequency shift in units of wavenumber ($cm^{-1}$). The region of the Raman spectra where most biological molecules have Raman peaks is from 500 to 2000 $cm^{-1}$. In contrast to fluorescence spectra, Raman spectra have sharp spectral features that enable easier identification of the constituent sources of spectral peaks in a complex sample. In the context of detecting the changes that cancerous tissues undergo, differences in the Raman spectral features that correlate to the increased nucleic acid content in neoplastic cells has observed [37].

The term "optical coherence tomography" or its acronym "OCT" refers to an interferometric, non-invasive optical tomographic imaging technique offering millimeter penetration (approximately 2-3 mm in tissue) with micrometer-scale axial and lateral resolution. In principle, the OCT is analogous to an optical version of ultrasound. While ultrasound images are formed by a transducer emitting ultrasonic pulses and then time gating detection of the tissue echoes, OCT images are formed by using an interferometer to correlate continuous wave light reflected from a reference mirror at a known distance with light reflected from a highly scattering tissue sample at an equivalent distance [14]. Both techniques essentially time gate a signal backscattered from the tissue, only OCT utilizes low-coherence interferometry rather than pulse-echo delay measurements due to the extremely high speed of light.

A low-coherence Michelson interferometer forms the backbone of an OCT system that includes a broadband laser source illuminating a 50/50 beamsplitter. The two arms of the interferometer in OCT are referred to as the reference and sample arms. In the reference arm, a moving mirror serves to reflect light back towards the beamsplitter for the purpose of correlation with the light backscattered from a biological specimen in the sample arm.

The backscattered light from the reference and sample arms interferes at the beamsplitter and is detector by a photodiode. The amplitude of the detected signal is essentially the reflectivity of the sample as a function of the reference mirror position, which is directly related to depth within the sample, while the axial point-spread function (PSF) is the autocorrelation of the reference electric field, which is equivalent to the Fourier transform of the broadband laser source spectrum. Because the point-spread function and laser spectrum are Fourier pairs, the broader the bandwidth of the laser, the better the axial resolution of the imaging system. Two-dimensional OCT images are built up by transverse scanning the sample beam across the sample and false-color coding the amplitude of the backscattered interference.

The term "point spread function" or its acronym "PSF" refers to the response of an imaging system to a point source or point object. The PSF in many contexts can be thought of as the extended blob in an image that represents an unresolved object. In functional terms it is the spatial domain version of the modulation transfer function. The degree of spreading (blurring) of the point object is a measure for the quality of an imaging system. In incoherent imaging systems such as fluorescent microscopes, telescopes or optical microscopes, the image formation process is linear and described by linear system theory. This means that when two objects A and B are imaged simultaneously, the result is equal to the sum of the independently imaged objects. In other words: the imaging of A is unaffected by the imaging of B and vice versa.

Telecentricity is a special property of certain multi-element lens designs in which the chief rays for all points across the object or image are collimated. For example, telecentricity occurs when the chief rays are parallel to the optical axis, in object and/or image space.

OVERVIEW OF THE INVENTION

The description will be made as to the embodiments of the present invention in conjunction with the accompanying drawings. In accordance with the purposes of this invention, as embodied and broadly described herein, this invention, in one aspect, relates to an apparatus combining Raman spectroscopy (RS) with an optical coherence tomography (OCT) system for non-invasive biochemical and structural evaluation of a target of interest of a living subject. The target of interest can be skin tissues, organ tissues, or the like.

Referring now to FIG. 1, the apparatus 100 includes a first light source 110, a second light source 115, a beamsplitter 150, a sample arm 160 and a reference arm (not shown).

The first light source 110 is adapted for generating a low coherence, broadband light that is characterized with a center wavelength, $\lambda 1$, and a spectral bandwidth, $\Delta$. The center wavelength $\lambda 1$ is in the range of about 1100-1500 nm, and the spectral bandwidth $\Delta$ is in the range of about 20-100 nm. The spectral bandwidth $\Delta$ determines the coherence length of the low coherence, broadband light. Light emitting diodes (LEDs), femtosecond lasers, broadband optical amplifiers or the like can be utilized to generate the low coherence, broadband light. The second light source 115 is adapted for generating Raman excitation light. The Raman excitation light is a monochromatic light having a Raman excitation wavelength, $\lambda 2$, in the range of about 600-1000 nm.

In one exemplary example shown below, the low coherence, broadband light is generated by a broadband optical amplifier light source (AFC Technologies, Inc., Ottawa, Canada) with a center wavelength at $\lambda 1=1310$ nm with a FWHM (full width at half maximum) spectral bandwidth $\Delta=61.3$ nm that corresponds to the coherence length of about 13 μm and an output power of 25.5 mW. The Raman excitation light is generated by a high power laser diode (Sacher Lasertechnik Group, Marburg, Germany) with the Raman excitation wavelength at about 830 nm.

The beamsplitter such as an OCT 2×2 fiber coupler 150, is optically coupled to the first light source 110 through an optical fiber 131 or other optical coupling means, and configured to receive the broadband light generated from the first light source 110 and to split the received broadband light into a reference light and a sample light therein. The reference light transmits through the reference arm and returns into the OCT 2×2 fiber coupler 150 along a reference optical path having a path length that is adjustable, while the sample light transmits through the sample arm 160 to the target of interest, which in response, scatters the sample light back to the sample arm 160. The backscattering light from the target of interest transmits through the sample arm 160 into the OCT 2×2 fiber coupler 150, and interferes with the returned reference light in the OCT 2×2 fiber coupler 150 to produce an interference signal containing information of the morphological details of the target of interest. The target of interest is placed in a sample stage 190 movable to allow the path length of the sample light to be varied or adjusted.

The sample arm 160 is optically coupled to the OCT 2×2 fiber coupler 150 and the second light source 115 and adapted for combining the sample light and the Raman excitation light, delivering the combined sample and Raman excitation light to the target of interest, collecting backscattering light and Raman scattering light returned from the target of interest in response to illumination by the sample light and the Raman excitation light, respectively, and directing the collected backscattering light and Raman scattering light in corresponding optical paths.

As shown in FIG. 1, the sample 160 includes a first collimating lens (C1) 121, a second collimating lens (C2) 122, a first dichroic mirror (D1) 123, a second dichroic mirror (D2) 124, a scanning member 125 and an objective lens 126.

The first collimating lens (C1) 121 is adapted for receiving the sample light from the OCT 2×2 fiber coupler 150 and collimating it into a first optical path 141. The second collimating lens (C2) 122 is adapted for receiving the Raman excitation light from the second light source 115 and collimating the received Raman excitation light into a second optical path 142. After the Raman excitation light is collimated, a band-pass filter (BP) 128 (Chroma Technology Corp., Rockingham, Vt.) having a center wavelength corresponding to the Raman excitation wavelength 830 nm is utilized to remove fluorescence or Raman signal generated from the fiber 132 optically coupled between the second light source 115 and the second collimating lens (C2) 122. The first collimating lens (C1) 121 and the second collimating lens (C2) 122 are substantially identical, which results in nearly identical beam diameters of the collimated sample light and Raman excitation light.

The first dichroic mirror (D1) 123 (Chroma Technology) is configured to receive the collimated sample light along the first optical path 141 from the first collimating lens (C1) 121 and the collimated Raman excitation light along the second optical path 142 from the second collimating lens (C2) 122, respectively, and transmit the received sample light into a third optical path 243 and reflect the received Raman excitation light into the third optical path 143, respectively, such that the transmitted sample light and the reflected Raman excitation light are co-aligned in the third optical path 143. The second dichroic mirror (D2) 124 (Chroma Technology) is configured to receive the combined sample and Raman excitation light along the third optical path 143 from the first dichroic mirror (D1) 123 and reflect it into a fourth optical path 144 towards the scanning member 125. In other words, the dichroic mirror (D1) 123 is adapted for reflecting the Raman excitation light, while transmitting light other than the Raman excitation light. The dichroic mirror (D2) 124 is adapted for transmitting the Raman scattering light, while reflecting light other than the Raman scattering light.

The scanning member 125 is configured to receive the reflected sample and Raman excitation light along the fourth optical path 144 from the second dichroic mirror (D2) 124 and telecentrically scanning the received sample and Raman excitation light onto the target of interest along a fifth optical path 145. The scanning member 125 includes micro-electronic mirrors (MEMS), micro-optoelectrical mirrors (MOEMS), galvanometer devices, rotation motors, translational motors or any combinations of them.

The sample and Raman excitation light scanned by the scanning member 125 are focused onto the target of interest by the objective lens 126 having a focal length, f. The objective lens 126 is placed at the fifth optical path 145 between the scanning member 125 and the target of interest such that the scanning member 125 is located at the focus of the objective lens 126, which ensures the sample and Raman excitation light are telecentrically scanned onto the target of interest. The objective lens (OL) 126 in one embodiment is a 1" diameter fused silica objective lens having the focal length about f=33 mm, (Newport-Spectra Physics, Irvine, Calif.). Using a fused silica objective lens instead of an achromatic doublet minimizes Raman silicon signal from the normal glass used in the achromatic doublet lens.

In response, the target of interest backscatters the sample light and the Raman excitation light in the forms of backscattering light and Raman scattering light, respectively, which are collected and focused to the scanning member 125 by the objective lens (OL) 126, and directed by the scanning member 125 along the fourth optical path 144 to the second dichroic mirror (D2) 124, from which the backscattering light is reflected by the second dichroic mirror (D2) 124 along the third optical 143 to the first dichroic mirror (D1) 123, and transmitted by the first dichroic mirror (D1) 123 along the first optical path 141 to the first collimating lens (C1) 121, while the Raman scattering light is transmitted by the second dichroic mirror (D2) 124 to a sixth optical path 146.

The backscattering light transmits to the OCT 2×2 fiber coupler 150 through the first collimating lens (C1) 121, and interferes with the returned reference light therein to produce an interference signal, which is acquired by an OCT detector 151 and processed in the form of OCT images.

A notch filter (NF) 129 centered at 830 nm is placed in the sixth optical path 146 for further filtering out elastically scattered light. The Raman scattering light is then optically coupled into a 100 μm low-OH fiber 135 (NA=0.22) by a 1" diameter fused silica lens (C3) 127 (f=62.9 mm) (Newport-Spectra Physics), and acquired a Raman spectrograph 155 and processed in the form of Raman scattering spectra. The Raman scattering spectra contains the information of biochemical content of the target of interest.

Because of the fact that Raman scattering is inherently a weak process and the low NA collection of the Raman scattering light may produce a signal with sub-optimal SNR, it is possible that the Raman collection parameters could be experimentally refined to produce better Raman scattering signal. In order to maximize the collection of Raman scattering light, increasing the diameter of the fiber 135 such that it is significantly greater than the spot size of the coupling lens C3 improves the Raman collection. While the theoretical diffraction limited spot size (assuming collimated incident light) for the coupling lens is about 3 μm, it will be larger than 3 μm in practice due to the divergence of the collected Raman beam. In collecting the Raman light, a 100 μm fiber is chosen to match the size of the slit within the existing spectrograph. Thus an increase in the size of the collection fiber would have to be accompanied by a corresponding increase in the size of the spectrograph slit in order to realize the increase in detected signal. This increase in slit size would result in an undesirable increase in the spectral resolution of the spectrograph. An alternative approach is to use a bundle of 100 μm fibers to fill the central portion of the spectrograph slit to maximize both acquired signal and spectral resolution.

As shown below, the combined system 100 is used to image and characterize a phantom that contains a highly Raman active element, like Acetaminophen tablet or naphthalene crystal, within a scattering medium such as a gelatin preparation. Such a phantom demonstrates the ability of the combined RS-OCT system to discern the exact nature of a structural anomaly within a sample. The system 100 is usable in acquiring combined RS-OCT data from normal and pathological in vitro skin samples to demonstrate the benefit of combined structural and biochemical analysis of skin pathologies.

Figure 2A:
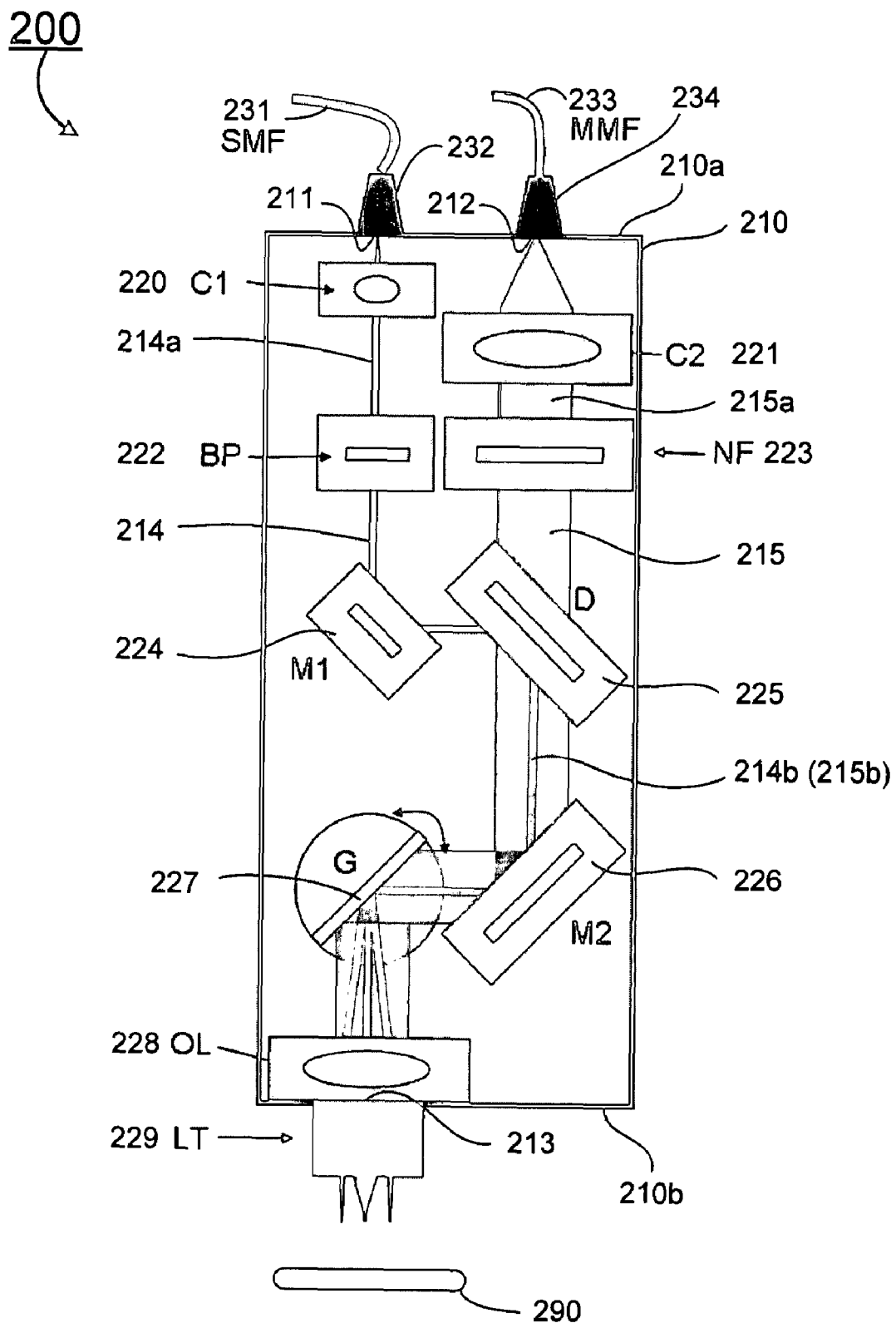
FIG. 2 shows schematically (A) a diagram of a combined RS-OCT handheld probe according to one embodiment of the present invention. In this exemplary embodiment, both OCT sample and Raman excitation light are optically coupled into a single single-mode fiber (SMF) and collimated by a single 0.55 NA collimation lens (C1). The collimated light is then passed through a custom dual-band pass filter (BP), and redirected to the galvanometer (G) by three mirrors (M1, D, and M2), which tele-centrically scans the light through the fused silica objective lens (OL) (D=1", f=33 mm) onto the target of interest (sample). A hollow adjustable lens tube (LT) is placed between the OL and the target of interest to allow precise control of the focusing plane within the tissue. Raman scattering light is collected and transmitted through a custom dichroic mirror (D), after which elastically scattered light is removed by a notch filter (NF). The Raman scattering light is then optically re-coupled into the multi-mode fiber (MMF) by means of a coupling lens (C2). (B) a perspective view of the handheld probe. For easy physician handling, the probe is mounted onto a pistol grip, inside of which the galvanometer magneto-motor is housed. The probe also has clamps mounted on the top of the device so that it can be stably mounted to a reticulated arm during the 30 sec Raman spectra acquisitions.

Referring to FIG. 2, a handheld probe 200 usable in a combined RS-OCT system for clinical imaging is shown according to one embodiment of the present invention. The handheld probe 200 is essentially a compact replica of the tabletop RS-OCT system, as shown in FIG. 1, with the most significant modifications being the coupling of both the OCT sample light and the Raman excitation light into the same single mode excitation fiber. After collimation of the two (OCT sample and Raman excitation) beams with the same collimation optics (D=6.3 mm, f=4.51 mm), the light is passed through a custom 0.5" diameter dual-band pass filter (Chroma Technology), which transmits both the OCT and Raman excitation bands and while again suppressing fiber fluorescence and induced Raman signal.

Specifically, the probe 200 has a casing 210 having a first end 210a and an opposite, second end 210b, and a first, a second and a third optical ports 211-213. The first and second optical ports 211 and 212 are located at the first end 210a of the casing 210 and the third optical port 213 is located at the second end 210b of the casing 210. The first and third optical ports 211 and 213 define a first optical path 214 therebetween and the second and third optical ports 212 and 213 define a second optical path 215 therebetween, respectively, inside the casing 210. Each of the first and second optical paths 214 and 215 has a first portion 214a, (215a) and a second portion 214b, (215b), where the second portions 214b, 215b of the first and second optical paths 214, 215 are substantially overlapped and proximal to the third optical port 213. A first optical connector 232 is optically coupled between the first optical port 212 and a single-mode fiber (SMF) 231. A second optical connector 234 is optically coupled between the second optical port 212 and a multi-mode fiber (MMF) 233.

The probe 200 further includes a collimation lens (C1) 220, a coupling lens (C2) 221, and an objective lens (OL) 228, a first, a second and a third mirrors (M1, D, M2) 224-226, and a scanning member (G) 227 for scanning a beam of light onto a target of interest 290 of a living subject at a speed. The beam of light comprises a broadband light and a monochromatic light.

The second mirror (D) 225 is a custom dichroic mirror configured to transmit the Raman scattering light and reflect light other than the Raman scattering light. The scanning member (G) 227 includes MEMS, MOEMS, galvanometer devices, rotation motors, translational motors or any combinations of them.

The objective lens (OL) 228 is an achromatic doublet objective lens or a fused silica objective lens.

As assembled, the collimation lens (C1) 220, the first mirror (M1) 224 are placed at the first portion 214a of the first optical path 214. The coupling lens (C2) 221 is placed at the first portion 215a of the second optical path 215 and proximal to the second optical port 212. The second and third mirrors (D, M2) 225, 226, the galvanometer (G) 227 (Cambridge Technology), and the objective lens 228 are placed at the overlapped second portion of the first and second optical paths 214, 215.

The galvanometer 227 has a small footprint within the probe casing of 1.18" and is capable of scanning at sufficiently high speeds for real-time OCT imaging. Both beams are then tele-centrically scanned and focused through a 33 mm focal length, 1" diameter fused silica objective lens 228. The objective lens 228 is statically mounted into threaded lens mount where the end of the mount closest to the patient has an adjustable lens tube (TB) 229 threaded inside. The lens tube (TB) 229 is hollow and serves as an adjustable spacer between the patient and the objective lens 228 allowing the focusing distance to be varied to examine different depths within the tissue in the optimal focus.

The backscattered Raman light is then isolated from the elastically scattered light through the custom dichroic mirror (D) 225, residual elastically scattered light is minimized with the 830 nm notch filter (NF) 223, and the Raman scattering light is then optically coupled to a multi-mode fiber (MMF). All the optics is mounted with flexure mounts 210 (Newport-Spectra Physics) to minimize the footprint and maximize stability. The magneto-motive driver of the galvanometer is housed within a pistol grip protruding from the bottom of the probe casing.

In operation, the beam of light is received from the first port 211 and collimated by the collimation lens (C1) 220 onto the first mirror (M1) 224, and redirected to the scanning member (G) 227 by the first, second and third mirrors (M1, D, M2), which telecentrically scans the beam of light through the objective lens (OL) 228 and the third optical port 213 onto the target of interest 290, the target of interest 290, in response to illumination by the broadband light and the monochromatic light, backscatters the sample light and the monochromatic light in the forms of backscattering light and Raman scattering light, respectively, which are collected through the third optical port 212 by the objective lens 228, and directed by the scanning member (G) 227 and the third mirror (M2) to the second mirror (D), from which the backscattering light is reflected by the second mirror (D) 225 and the first mirror (M1) 224 onto the collimation lens 220 and transmitted by the collimation lens 220 to the first optical port 211, while the Raman scattering light is transmitted through the second mirror (D) and the coupling lens (C2) to the second optical port 212.

Figure 2B:
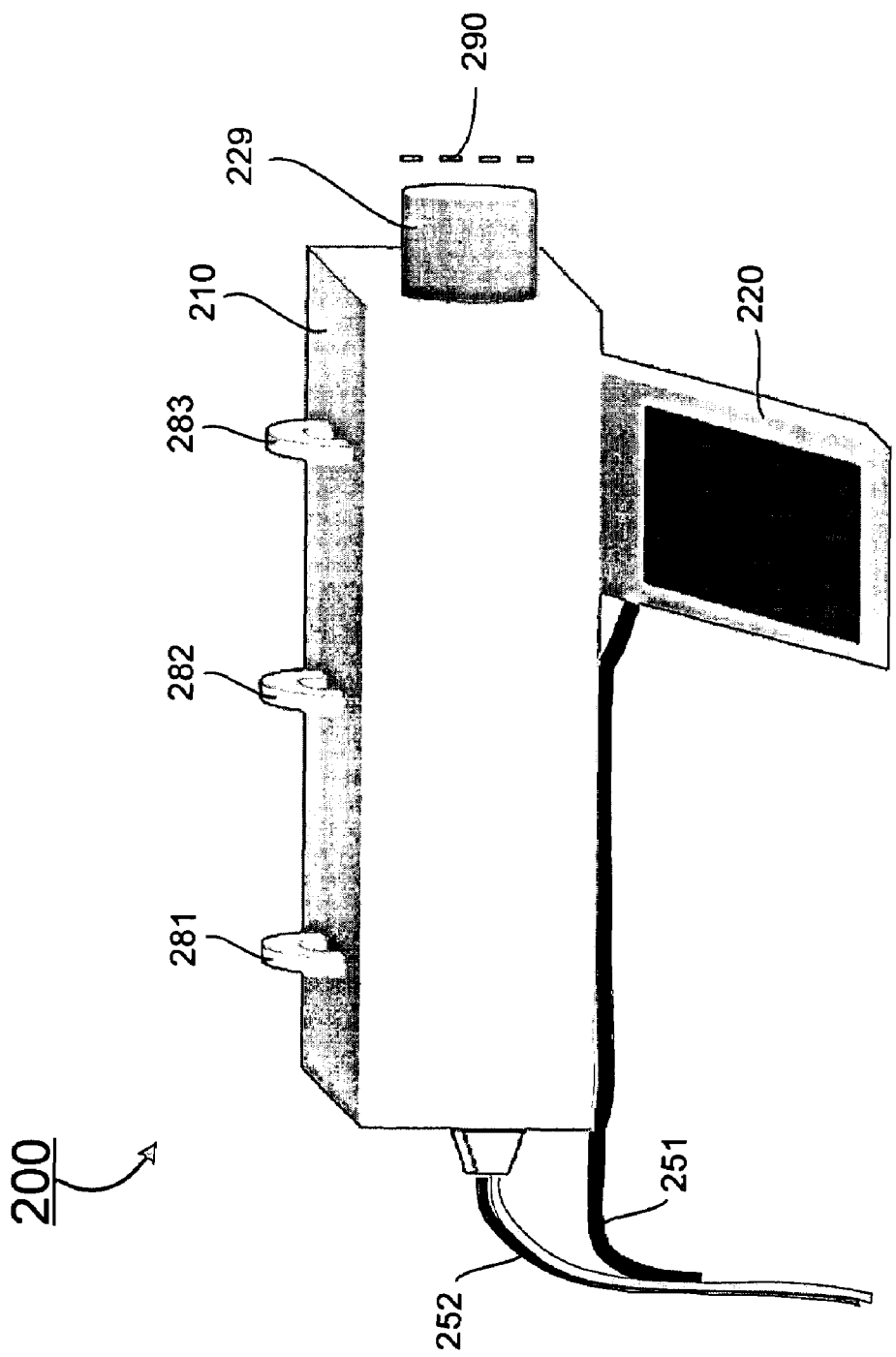

As shown in FIG. 2B, on the top of the probe casing 210 a set of three clamps 281-283 are attached for clamping the probe 200 with a 0.5" diameter metal reticulated arm. This allows for stable placement of the probe 200 over the course of a Raman spectra acquisition, which may last approximately 30 seconds. The pistol grip 220 gives the physician easy control of the probe 200 and the adjustable lens tube (TB) 229 allows for easy examination of the questionable skin lesion at the exact point of interest. The galvanometer control wire 251 along with the fiber optic cables 252 is bundled together in an umbilical cord back to the main system control unit, which is placed on a cart. The entire casing of the device is machined from lightweight aluminum to minimize weight.

In one embodiment, the handheld probe may be modified by replacing M2 with a low pass filter that transmits the visible spectrum and reflects the infrared. A regular CCD camera may be placed on the side of the probe casing while a ring LED is placed at the front of the adjustable lens tube for illumination.

Because the OCT image is acquired over a depth of roughly 2 mm's, only the central portion of the image plane occurs at the beam waist, while the regions deeper and shallower in the image plane are partially out of focus. This results in the decrease of the lateral resolution and the degradation of OCT images. This may be overcome by utilizing a MOEMS scanning mirror. When a large voltage is applied to the mirror it deforms enough to change the focal length of the system. The focal length of the system can then be tracked to follow the A-scan acquisition so as to ensure that the entire A-scan remains in focus. Such a configuration of the probe 200 is achieved by replacing the galvanometer with the objective lens and then placing the MOEMS mirror on the same optical axis as M2 and G. In order to achieve a 5 mm OCT B-scan image width and still largely avoid off-axis lens effects, a 1" diameter final objective lend is utilized.

Figure 3:
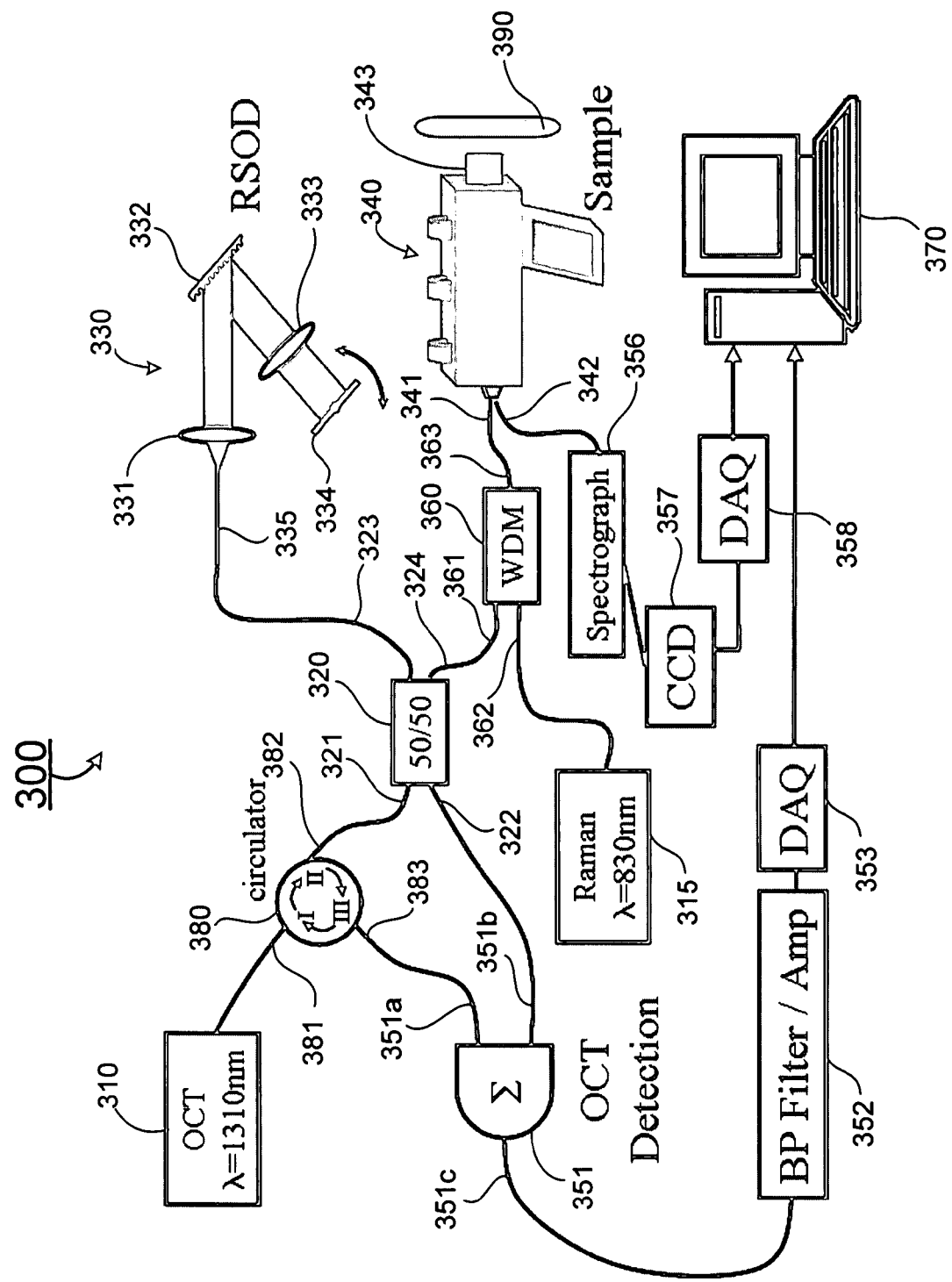
FIG. 3 shows a Raman spectroscopy-optical coherence tomography (RS-OCT) system according to another embodiment of the present invention. One of critical elements involved in integrating the RS and OCT systems is a custom built wavelength division multiplexer (WDM) inserted into the sample arm that enables coupling of the 830 nm Raman excitation light and the 1310 nm OCT light into the same fiber. OCT reference delay scanning is achieved with a RSOD, and detection with the dual balanced detection configuration that incorporates an optical circulator into the source arm. Acquisition of the Raman spectra is achieved through a spectrograph and high sensitivity thermoelectrically cooled CCD camera. Two separate data acquisition cards (DAQ) control digitize the data, where it is processed and displayed on a single desktop computer. The entire system is mounted onto a pushcart for easy transportation.

Referring now to FIG. 3, an integrated RS-OCT system 300 is shown according to one embodiment of the present invention. The RS-OCT system 300 has a first light source 310 for generating a broadband light with a center wavelength, $\lambda 1=1310$ nm, and a second light source 315 for generating a monochromatic light at a single wavelength, $\lambda 2=830$ nm.

An optical circulator 380 having three ports 381-183 is optically coupled to the first light source 310, a beamsplitter 320 and an OCT detector 351, respectively. The optical circulator 380 is configured such that when an optical signal is fed into and received by one of the three ports 381-183, the fed optical signal is transferred from the receiving port to a predetermined one of the other two ports port. In this configuration as shown in FIG. 3, the broadband light generated from the first light source 310 is fed into port 381 and output from port 382 of the optical circulator 380. The broadband light output from port 382 of the optical circulator 380 is then fed into and received by the beamsplitter 320 through its first port 321. The beamsplitter 320 splits the received the broadband light into a reference light and a sample light.

A reference arm 330 is optically coupled to the beamsplitter 320 through its third port 323 for receiving the reference light and returning the received reference light into the beamsplitter 320. As shown in FIG. 3, the reference arm 330 includes a rapid scanning optical delay (RSOD) for varying the optical path length. The RSOD has a fiber optic collimator 331, a grating 332, a phase control delay lens 333 and a galvanometric mirror 334 placed at the optical path and configured such that in operation, the reference light is received by the fiber optic collimator 331 and collimated onto the grating 332, and redirected by the grating 332 to the galvanometric mirror 334 through the phase control delay lens 333, which scans the reference light back towards the fiber optic collimator 331 through the phase control delay lens 333 and the grating 332, thereby varying the optical path length of the reference light propagating through the reference arm 330. Other types of the reference arm, such as a reference arm having a movable mirror can also be utilized to practice the present invention.

One of the critical elements of the integrated RS-OCT system according the present invention is a custom built wavelength division multiplexer (WDM) 360 (Optics For Research, Co.) that is optically coupled to the beamsplitter 320 through its fourth port 324, the second light source 315 and the probe 340 for receiving the OCT sample light and the Raman excitation light, multiplexing them into a single fiber 363, and delivering the multiplexed OCT sample light and Raman excitation light to the probe 340 through its first port 341. The WDM 360 is configured to receive the backscattering light from the probe 340 and return it into the beamsplitter 320.

Another critical element of the integrated RS-OCT system is a probe 340 as disclosed above. The probe 340 has a working end placed 343 proximal to the target of interest 390, and is optically coupled to the WDM 360, which in turn is optically coupled to the beamsplitter 320 and the second light source 315. The probe 340 is adapted for receiving the multiplexed OCT sample light and Raman excitation light through its first port 341 from the WDM 360, delivering them from the working end 343 to the target of interest 390, and collecting from the working end 343 a backscattering light and a Raman scattering light that are obtained from the interaction of the OCT sample light and Raman excitation light the target of interest 390, respectively.

The collected backscattering light is transmitted by the probe 340 through its first port 341 into the WDM 360 through its third port 363 and then transmitted by the WDM 360 into the beamsplitter 320. By adjusting the length of the reference optical path, the backscattering light interferes with the returned reference light in the beamsplitter 320 to generate an interference signal with an interference pattern. The interference signal is detected by an OCT detector 351 having its first and second ports 351a and 351b respectively connected to the third port 383 of the optical circulator 380 and the second port 322 of the beamsplitter 320. In one embodiment, the OCT detector 351 includes a dual-balanced InGaAs 80 MHz detector (New Focus Corp., San Jose, Calif.), which is in communication with a band pass (BP) filter or amplifier 352. The detected interference signal provides an OCT image containing the information of morphological details of the target of interest 390.

The collected Raman scattering light is transmitted by the probe 340 through its second port 342 into a spectrograph 356 that acquires the Raman scattering light along with a thermoelectrically cooled, deep-depletion, back-illuminated CCD 357 (Roper Scientific Inc., Duluth, Ga.). The acquired Raman scattering light is processed into a frequency spectrum containing the information of biochemical contents of the target of interest 390. Specifically, the frequency spectrum of the Raman scattering light has a plurality of intensity peaks at a plurality of wavelengths, where each intensity peak is associating with a specific biochemical content of the target of interest.

Multi-function data acquisition (DAQ) cards 353 and 358 are used to digitize the acquired OCT images and Raman scattering spectra. A controller (computer) 370 is in communication with the DAQ 353 and 358 and programmed to correlate the OCT images with the Raman scattering spectra and determine the structures and biochemical content of the target of interest from the correlated OCT images and Raman scattering spectra.

Figure 4:
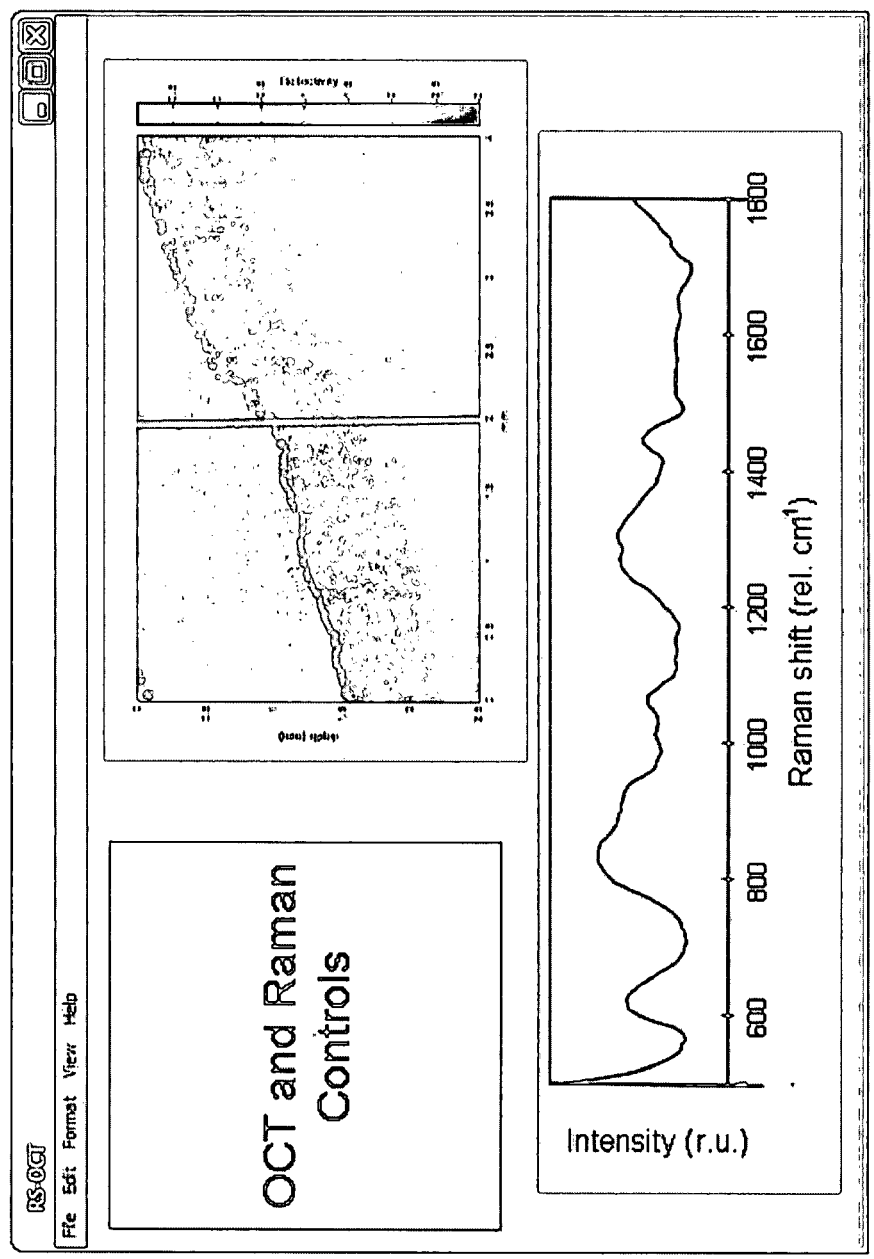
FIG. 4 shows an application interface for software control of the integrated combined RS-OCT system according to present invention. The application interface includes the capability for the user to control OCT imaging depth and width, as well as Raman spectra acquisition time and position through a graphical user interface.

The OCT images and the Raman scattering spectra are visualized in a display associated with the controller 370, as shown in FIG. 4.

Additionally, the scanning of the RSOD and sample arm galvanometer are also controlled by the analog output capabilities of the multi-function DAQ 353 used to acquire the OCT images (not shown).

In one embodiment, an integrated windows based graphical software control application is utilized to simultaneously control OCT imaging and Raman spectral acquisition and present the data for side-by-side comparison and analysis. A general layout of the software interface is shown in FIG. 4. The application is developed in either the LabView, Visual C++ development environments or the like. The user is able to control clinically relevant OCT imaging parameters such B-scan width and imaging depth, in addition to the clinically relevant Raman spectra acquisition parameter of integration time. The system continuously acquires OCT images in real-time, and upon the determination of the location for acquisition of the Raman spectra, the user selects the line in the OCT image, and the scanning mirror will stop the beam at the given position while the Raman spectra is acquired. The program incorporates the automated modified polynomial fit fluorescence and background subtraction algorithm [37]. Additionally, the software could contain elements of the resultant Raman discrimination preliminary findings, such as standard error bars for different tissue types in addition to image libraries of OCT images acquired from different tissue types.

Potential difficulties in acquiring Raman spectra with similar sampling volume characteristics could arise when selecting lines towards the far peripheral regions of the OCT image due to off-axis focusing effects. The influence of these off-axis focusing effects is determined with benchmarking techniques to determine if the user selection of Raman spectra acquisition location is in fact a viable method. If not, the physician places the pathological region of interest squarely in the center of the OCT image plane before acquiring the Raman spectra.

The integrated RS-OCT system according to the present invention can be a viable clinical tool that is employed to acquire combined Raman spectroscopy-OCT data sets from in vitro normal and pathological as well as in vivo normal and interesting skin regions for the analysis of human tissues and serve as a major step towards the entirely optical, completely non-invasive differential diagnosis of skin pathologies.

One aspect of the present invention relates to a method for evaluating morphological details and biochemical contents of a target of interest of a living subject. The method includes the following steps: at first, a broadband light and a monochromatic light are generated. The generated broadband light is split into a reference light and a sample light. Then, the sample light and the monochromatic light are co-aligned into an optical path leading the sample light and the monochromatic light to the target of interest. The co-aligned sample and monochromatic light is telecentrically scanned onto the target of interest along the optical path, which in response, backscatters the sample and monochromatic light in the form of backscattering light and Raman scattering light, respectively. The backscattering light returned from the target of interest interferes with the reference light to provide an interference signal. The interference signal and the Raman scattering light are acquired and processed in the forms of OCT images containing information of morphological details and frequency spectra containing information of biochemical contents of the target of interest, respectively. The OCT images and the frequency spectra are further correlated so as to determine the morphological details and biochemical contents of the target of interest.

To evaluate the feasibility of the above-disclosed RS-OCT system for performing entirely optical, non-invasive differential diagnosis of normal and cancerous skin lesions, a significant amount of clinical experience needs to be gained by both the researchers and the clinicians in interpreting OCT images of various skin types, in statistically discriminating between the various types of skin pathologies based on the Raman spectra, as well as the finer points of practically using optical probes in dermatological clinical setting.

To gain the experience and data, a handheld OCT probe is designed to for an individual OCT system so that experience can be gained by both the researchers and the physicians in relation to interpreting OCT images of the skin and practically using the handheld OCT imaging probe. Furthermore, Raman scattering spectra are acquired from various skin lesions with the existing clinical handheld Raman probe currently being used for cervical studies in order to begin building up a volume of Raman spectra from the skin to be used for development of discrimination algorithms for normal, and cancerous tissues.

Figure 5:
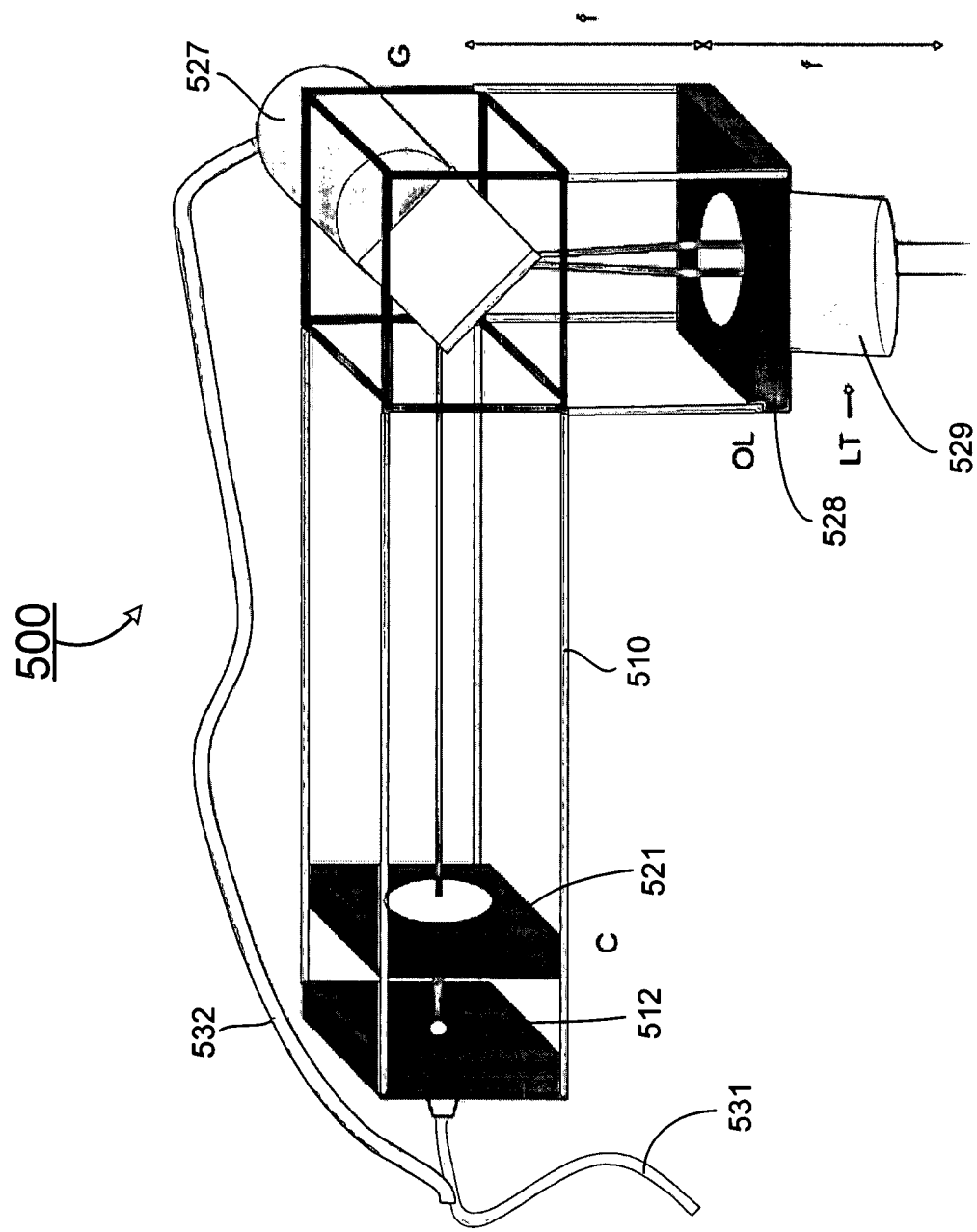
FIG. 5 shows an OCT sample probe according to one embodiment of the invention. The handheld OCT sample probe includes a collimation optic lens (C), a scanning galvanometer, and an objective lens (OL). The collimation optic lens (C) is mounted in a cage and an adjustable lens tube (LT) is placed between the patient and the objective lens to stabilize the imaging and allow for control of sample axial positioning.

The handheld probe 500 for an individual OCT system that allows the researchers and physicians to gain experience in clinical OCT imaging is shown in FIG. 5. The OCT beam 512 is collimated by a collimating lens 521, and tele-centrically scanned by a single galvanometer 527 through a 1" diameter, f=35 mm focal length achromatic doublet objective lens 528. An adjustable lens tube 529 is screwed into the front of the lens mount to allow for adjustment of the probes working distance so that the focal distance can be matched to the depth of the structure of interest in the tissue. All optics is mounted with commercially available cage-based optical mounts 510 (Thor Labs). The galvanometer control cable 532 and the fiber optic cable 531 are bundled together and fixed to the probe 500, and the OCT system hardware are rack mounted and placed on a pushcart for easy transportation to and from the clinic. Optically, a custom machined heat-sink (not shown) is mounted onto the probe 500 to allow for integration into the cage system and prevent overheating.

The Raman probe system employs a 785 nm excitation light delivered to the tissue via a fiber optic probe for excitation and collection. A ring is machined with an inner diameter equal to the Raman probe so that after imaging, a mark can be made at the site the spectra are acquired from for accurate histology.

The two probe systems are clinically employed to perform regular OCT imaging and Raman spectroscopic analysis of normal and pathological skin conditions.

A protocol submitted to the Vanderbilt IRB to gain approval for a study that enrolls patients presenting with suspected cancerous lesions who undergo biopsy for pathological evaluation is as follows. Each optical modality examines approximately 30 or more patients and an effort is made to acquire an even distribution of images/spectra from the patients with suspected BCC, SCC, and melanoma lesions. Both Raman spectroscopy results and OCT images are compared to the gold standard of the histological findings. Ideally, patients undergo OCT imaging, Raman spectroscopy, and biopsy all at the same site within the same patient in order to develop an idea of how the three diagnostic methods relate, however it may not be feasible to have both systems available on in the clinic on a regular basis, as the Raman probe is already committed to the cervical study.

Upon initial evaluation of a suspected cancerous site by the physician, the site is cleaned with an alcohol swab and the OCT imaging probe is scanned such that a continuous stream of OCT images are recorded over the entire suspicious area. Aligning the OCT image place exactly with the biopsy location proves to be difficult and time consuming, so an approach that determines the tissue morphologies after the fact may be the most effective. Previous work in skin [35] has shown that paired analysis of Raman spectra (normal and suspicious) produce the best results in discrimination. Therefore, three Raman spectra from normal tissue adjacent to the lesion are acquired in addition to three Raman spectra from the lesion of interest. The guiding ring is then used to create a mark on the lesion to guide histology. Adhesive tape may be used to hold the ring in place during the procedure. Additionally, a normal photograph of the skin lesion is taken for gross analysis of the lesion after the fact. Finally, background spectra in the analysis room are acquired to remove any environmental ambient noise. Before each day of data collection, the Raman probe is calibrated using a Neon-Argon lamp and Raman standards Acetaminophen and naphthalene.

Data analysis is performed off-line or online for both the Raman spectra and the OCT images. Histological evaluation of the excised tissues is performed by trained pathologists in the Skin Diseases Core. OCT image processing entails simply employing a spatial averaging filter on the order of the physical resolution of the system to minimize speckle noise. After histology, the OCT images are viewed in order to determine the degree of correlation between the two images and to note any patterns observed. Raman spectra are processed by polynomial fluorescence background subtraction, and mean scaled to allow for paired analysis. Initially, they are qualitatively compared to the findings from previous confocal studies of human skin [35]. After a sufficient number of samples from each tissue type (10 normal, BCC, SCC) are obtained, statistical analysis of the spectra is performed using a student's t-test along the wavenumber axis to determine regions where significant spectral differences occur. Spectra classification is performed with logistic discriminant analysis, and the discrimination algorithms performance is evaluated using leave-one-out cross validation. In anticipation of the large number of data sets to be collected as work in discrimination of pathological skin lesions continues, a data reduction technique such as principal component analysis is evaluated. Both Raman spectroscopy results and OCT images are compared to the pathological findings as a gold standard.

The present invention, among other things, discloses a combined Raman-spectroscopy-OCT with a handheld probe for discrimination of BCC, SCC, and melanoma from normal suspicious skin lesions. Significant progress is made towards the clinical implementation of Raman spectroscopy in skin cancer, as well as initial experience gained at Vanderbilt University in the diagnostic potential of OCT in skin cancers. In a broader sense, the present invention demonstrates significant progress towards the entirely optical, completely non-invasive differential diagnosis of skin pathologies.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Demonstration of the Complimentary Nature of Raman Spectroscopy and Oct

The fundamental objective of this example is to validate the utility of combined biochemical and structural analysis of biological tissues with Raman spectroscopy and OCT. To demonstrate the underlying concept in practice an in vitro human skin sample obtained from the Vanderbilt University tissue bank is evaluated with both individual OCT and Raman spectroscopy systems.

Figure 6:
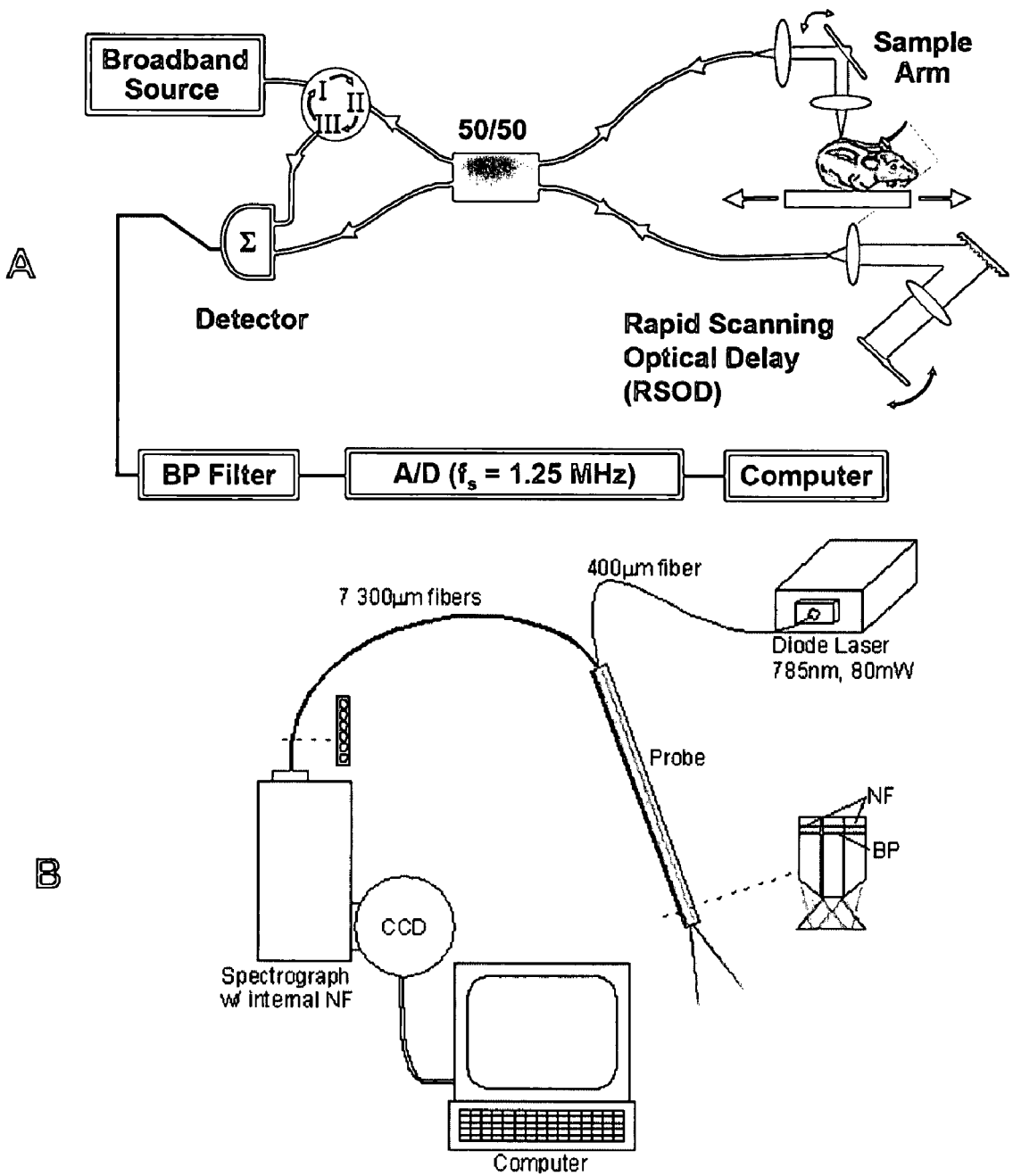
FIG. 6 shows individual OCT and Raman spectroscopy systems. (A) an individual OCT system, and (B) an individual Raman spectroscopy system.

A schematic diagram of the individual OCT system is shown in FIG. 6A. A broadband optical amplifier light source (AFC Technologies, Inc.) with a center wavelength at 1310 nm with a FWHM spectral bandwidth of 61.3 nm (a coherence length of about 13 µm) and an output power of 25.5 mW. The broadband source illuminates a fiber-based Michelson interferometer in which reference delay scanning is achieved with a rapid-scanning optical delay line [36]. Scanning of the sample beam across the specimen is achieved with a galvanometer in the sample path. The sample objective lens had a focal length of 35 mm, which corresponds to a spot size of 25 µm in the focal plane. The interferometric signal was then detected with an 80 MHz dual-balanced detector (New Focus Corp.), band-pass filtered, and then directly digitized (National Instruments Corp. Austin, Tex.) at 1.25 MHz.

The individual Raman spectroscopy system shown in FIG. 6B is the same system used for the current cervical study underway at Vanderbilt Medical Center. The RS system utilizes a 785 nm laser diode for Raman excitation and 7 angle-polished 300 µm fiber arranged in a 7 around 1 configuration for collection of the Raman scattering light. The fibers are then aligned vertically upon input into the detection spectrograph. The spectra are acquired by a thermo-electrically cooled, deep depletion, back illuminated CCD camera and recorded onto a laptop computer for processing.

A frozen (−80° C.) in vitro skin sample from a dark skinned 50 year old Black female was thawed to room temperature, and then Raman spectra were collected, followed by OCT imaging. Although the tissue sample appeared relatively homogenous, care was taken to co-align the location of the Raman spectral acquisition and the OCT imaging plane. Acquisition time for the Raman spectra was 1 sec and 3 spectra were averaged to create the characteristic Raman signature. Raman spectra were calibrated using the atomic emission lines of a Neon-Argon lamp and Raman standards acetaminophen and naphthalene. OCT images were acquired at 1.5 frame/second and processed in software to remove the interferometric carrier fringes and logarithmically scale the signal intensity. Due to the extreme melanin content of the skin sample, an optical clearing solution of 50% glycerol was applied to the surface of the tissue to allow visualization of the epidermal/dermal interface. 3 OCT image frames were averaged to produce the characteristic OCT image. After imaging, the tissue section was preserved in formalin until it could be processed for histology.

Figure 7:
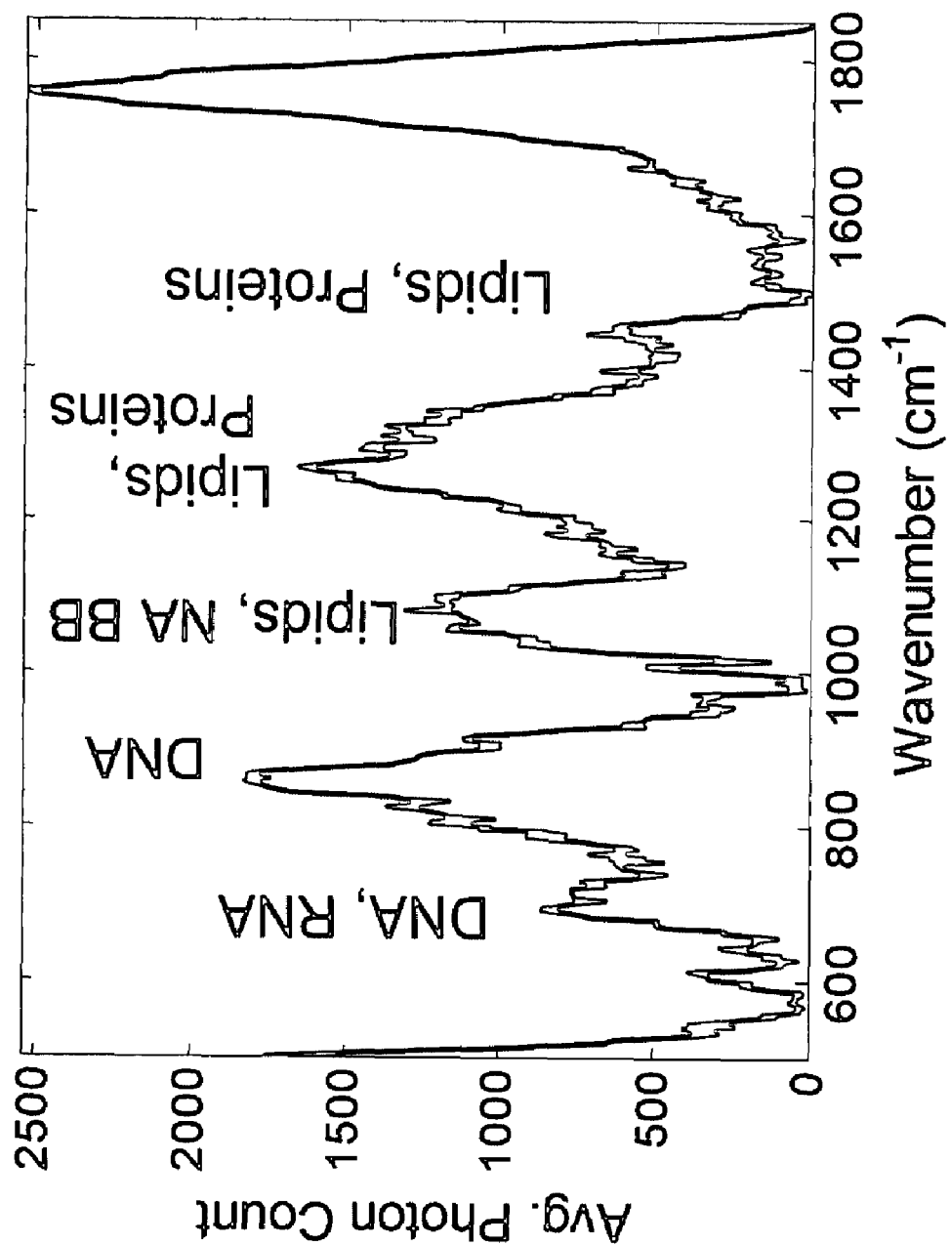
FIG. 7 shows Raman Spectra from in vitro skin sample. Raman spectra shows peaks characteristic of the molecular bonds present in the scattering molecules in normal skin. These molecules include, DNA, RNA, lipids, proteins, and the nucleic acid backbone (NA BB).

As shown in FIG. 7, the collected Raman spectra show features typical in normal skin. The peak in the 786 cm$^{-1}$ wavenumber region is characteristic of $PO_2$ symmetric stretching, indicative of DNA and RNA. The larger peak in the 830 cm$^{-1}$ wavenumber region corresponds to $PO_2$ asymmetric stretching, which is indicative of DNA and tyrosine. 1085 cm$^{-1}$ is caused by symmetric stretching of $PO_2$, which is common in lipids and the nucleic acid backbone. The large peak in the 1304 cm$^{-1}$ region is due to the amide III band present in proteins, as well as lipids. The smaller peak in the 1445 cm$^{-1}$ region is due to $CH_2$ deformation in proteins and lipids.

Figure 8:
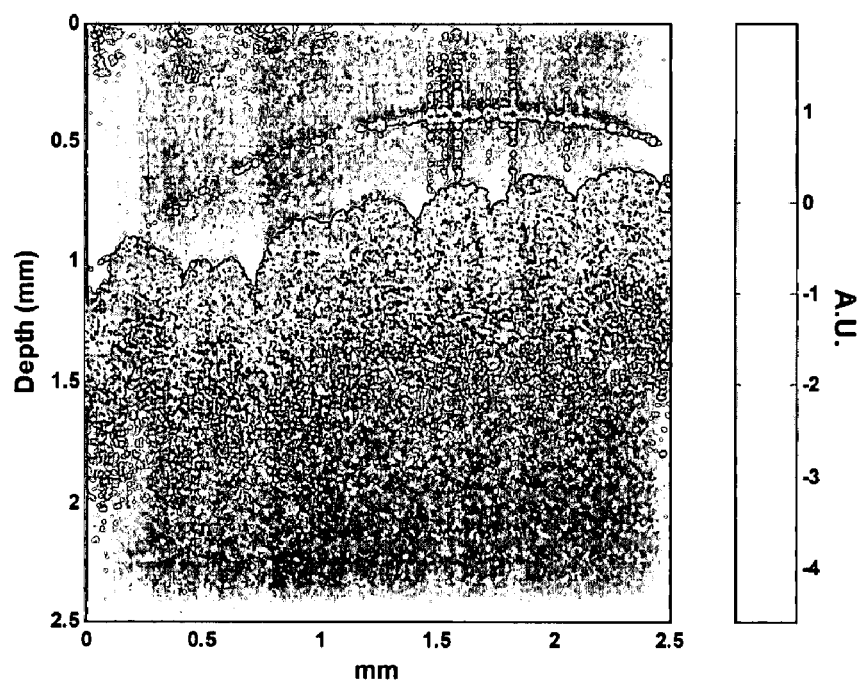
FIG. 8 shows an OCT image of in vitro skin sample. The epidermis appears as the yellow colored region at the surface of the tissue. Intensity scale is in arbitrary units (A.U.) of reflectivity. Arc above the tissue surface is the glycerol solution.
Figure 9:
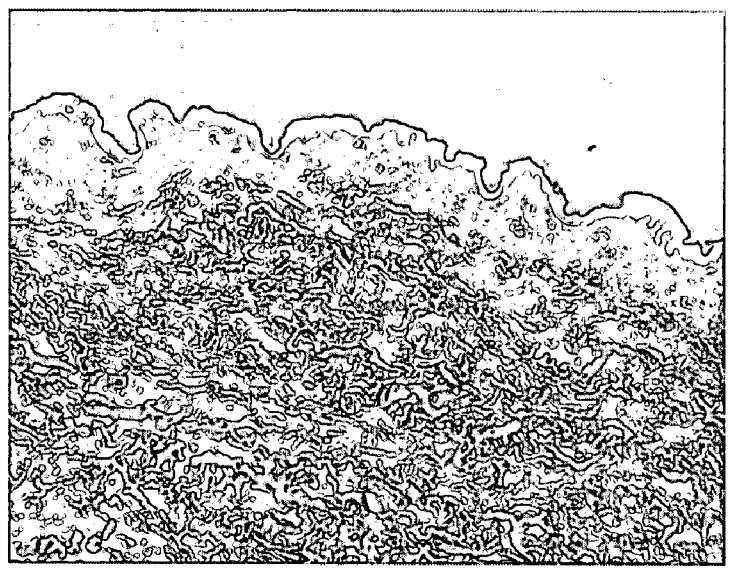
FIG. 9 shows histology of in vitro skin sample. The dark pigmentation of the epidermis is due to the high melanin concentrations.

OCT images taken in nearly the same location are able to resolve the epidermal and dermal layers in the skin, with the epidermal layer appearing as a light yellow in the false color image, as shown in FIG. 8. When examining the corresponding histology of tissue sample, as shown in FIG. 9, the epidermis can be seen as the dark band at the tissue surface while the dermis is the layer just beneath it.

Histology image was taken at 10× zoom, so the distance scales of the OCT and histology images are not matched.

The observation from these results is that neither the Raman spectra, nor the OCT image is capable of completely elucidating the state of the tissue being evaluated individually. While the Raman spectra is capable of providing specific information related to the biochemical content of the sample, no structural information can be ascertained. On the other hand, the OCT image is capable of providing a general image of the tissue microstructure, however there is a fundamental lack of information related to the biochemical composition of the sample. The ability to use both of these optical diagnostic techniques in a complimentary fashion could result in the development of an optical device with superior diagnostic functionality than either technique alone.

Example 2

Combined Raman Spectroscopy—OCT System

While OCT is a powerful technique capable of identifying structural anomalies in scattering samples, it is incapable of determining the composition of structural in-homogeneity. Raman spectroscopy, on the other hand, is a powerful technique for evaluating the biochemical composition of a scattering sample, however it is unable to practically perform and sort of spatial mapping in vivo due to the fundamentally weak nature of Raman scattering. In addition, the weak nature of Raman scattering makes probe placement a critical variable when using Raman spectroscopy to evaluate spatially confined tissue structures in vivo. This example demonstrates the ability of a combined Raman Spectroscopy-OCT device to confirm the suspected chemical composition of a scattering structure in an OCT image, and guide the placement of a Raman probe beam such that optimal Raman backscatter is collected. This is achieved by analyzing a scattering phantom consisting of a tablet of acetaminophen (which is strongly Raman active) immersed in a solid scattering gelatin medium.

The scattering phantom was created by placing a half tablet of acetaminophen in a solution of primarily gelatin and water, with a small volume (2%) of 1 µm polystyrene micro-spheres. The solution was rapidly cooled by placing it in a −80° C. freezer to minimize the amount of acetaminophen that entered the solution. Upon hardening the location of the acetaminophen tablet could be vaguely distinguished with the naked eye.

The combined RS-OCT system used is disclosed above. The optical configuration simply involved modifying the existing OCT system's sample arm to allow co-alignment of a Raman excitation beam with the OCT sample beam and collection of the Raman scattered light for detection by an spectrograph currently used for the confocal Raman system, as shown in FIG. 1.

The system allows for the co-linear delivery of the OCT sample beam and the Raman excitation beam ($\lambda$=830 nm) through the dichroic mirror D1. Dichroic mirror D2 reflects both the OCT band and the Raman excitation band while transmitted the entire Raman scattered biochemical fingerprint region for 830 nm excitation. The light was focused on the sample with an achromatic doublet objective lens (D=25.4 mm, f=35 mm). The focus of the OCT sample beam was found to be at a depth of 1.5 mm. The Raman beam's focus was assumed to be roughly in the same position. Raman scattered light was optically coupled using a fused silica lens (D=25.4 mm, f=40 mm). The spectrograph used in this was tuned for an excitation wavelength of 825 nm. Raman spectra were acquired with acquisition times of 60 sec with the galvanometers zeroed (corresponding the center of the OCT image), and analyzed un-processed. OCT images were acquired at 2 frames/second, and also analyzed un-processed. Demonstration of OCT's ability to guide optimal Raman spectra acquisition was demonstrated by acquiring a spectra from a fixed beam position that visually appeared to be exciting tablet, but was known to be slightly offset from the center of the tablet based on the OCT imaging. The sample was then adjusted to center the tablet both laterally and in depth using OCT, and a second Raman spectrum was acquired. The ability of Raman spectroscopy to discern the biochemical composition of the sample was demonstrated by comparing the optimally collected Raman spectra to the known Raman spectra for acetaminophen.

Figure 10:
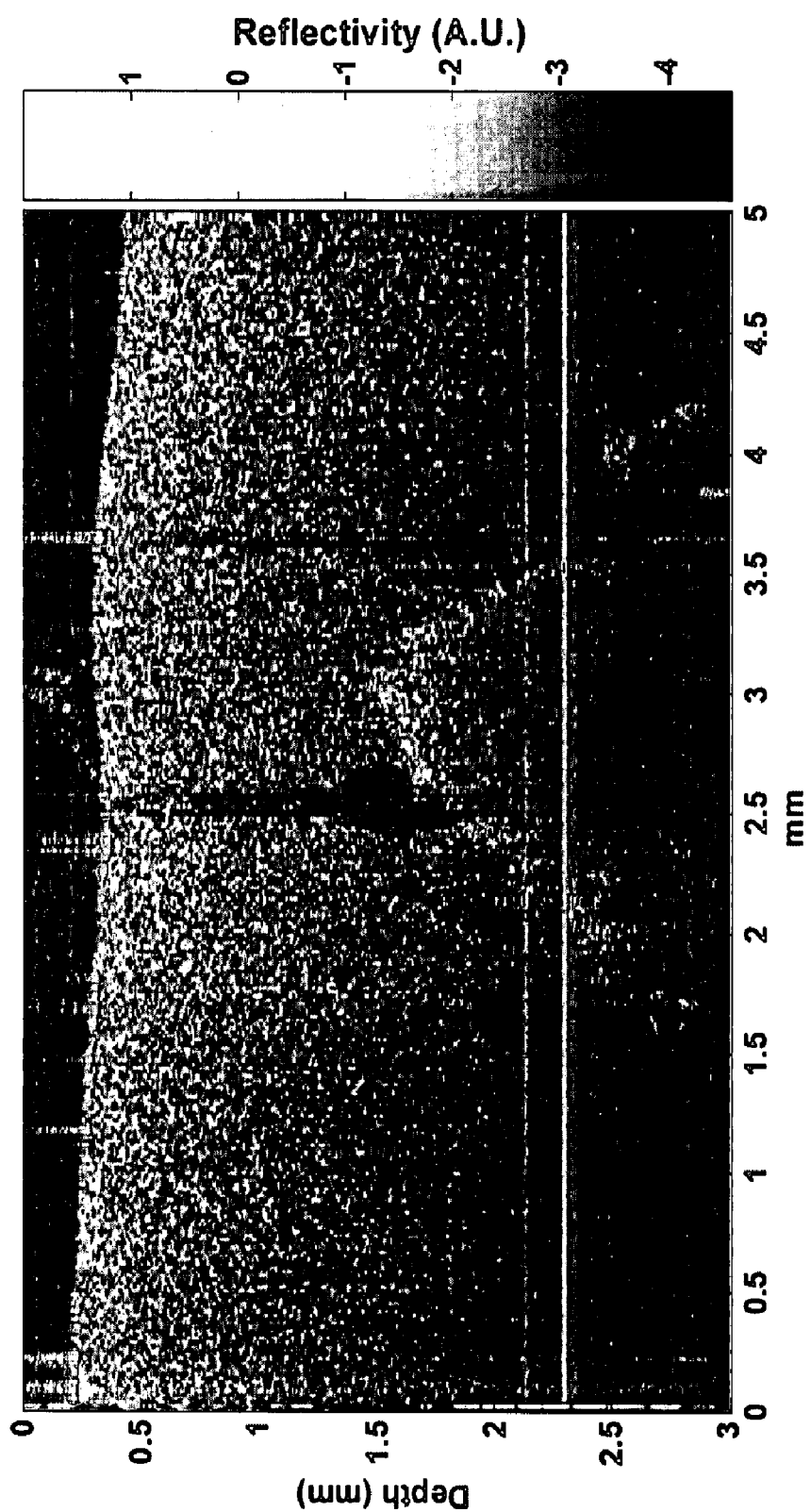
FIG. 10 shows an OCT image of acetaminophen tablet in gelatin phantom.

As shown in FIG. 10, OCT images of the phantom show a clearly visible tablet within the medium at a depth of approximately 1.25 mm.

Figure 11:
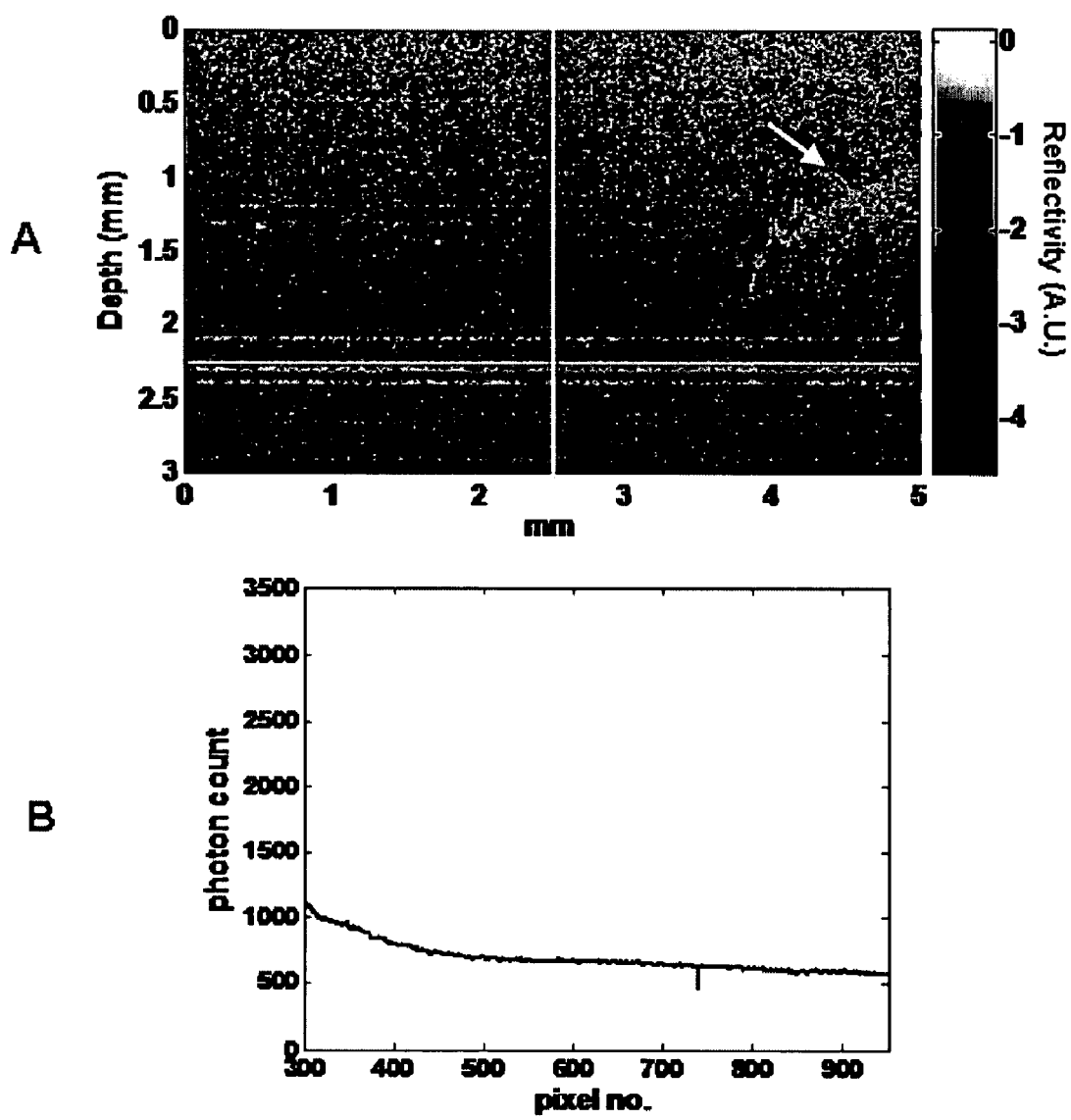
FIG. 11 shows an offset OCT image and Raman Spectra of Acetaminophen phantom according to one embodiment of the present invention. OCT image shows the tablet (arrow) (A), while the Raman spectra (B) acquired at the central position of the OCT image (indicated by the yellow line in the OCT image) shows no significant spectral features.
Figure 12:
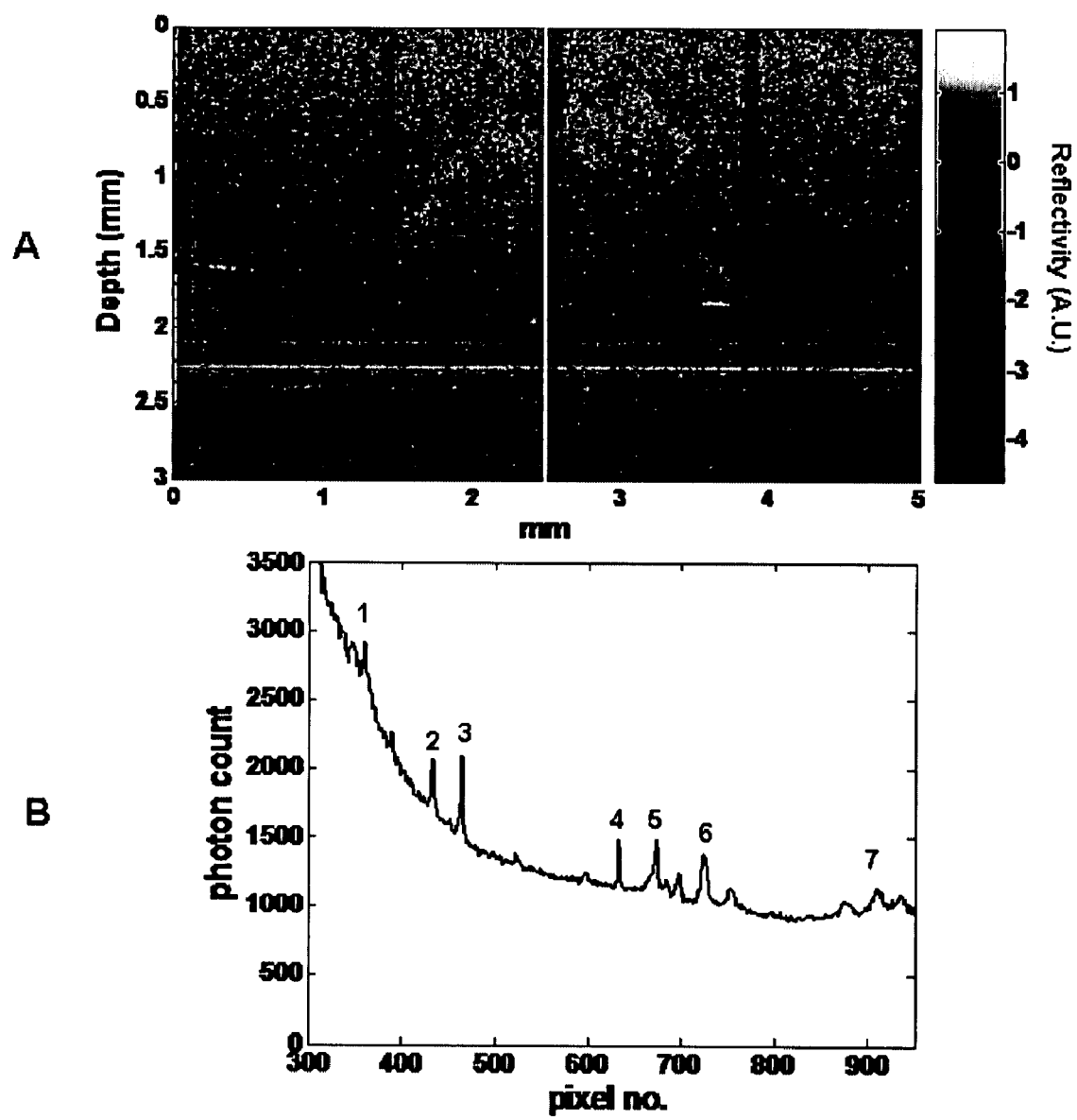
FIG. 12 shows a centered OCT image and Raman Spectra from Acetaminophen Phantom. OCT image (A) shows the tablet clearly centered. The Raman spectrum (B) acquired from the central scan of the OCT (yellow line in OCT) shows peaks not seen in the offset spectrum.

The sample was slightly misaligned, such that the edge of the tablet could be seen in the peripheral region of the OCT image, as shown in FIG. 11A, and the corresponding Raman spectra was acquired and shown in FIG. 11B. The only signal present in the unprocessed Raman spectra was the laser line, minimal background fluorescence, and stray light (all of which were due to sub-optimal nature of the system components). The sample was then centered in the OCT image both laterally, and in depth (focus of the beams was roughly at z=1.5 mm), as shown in FIG. 12A and the corresponding Raman spectra showed the presence of distinct peaks not seen in the misaligned spectra, as shown in FIG. 12B.

Figure 13:
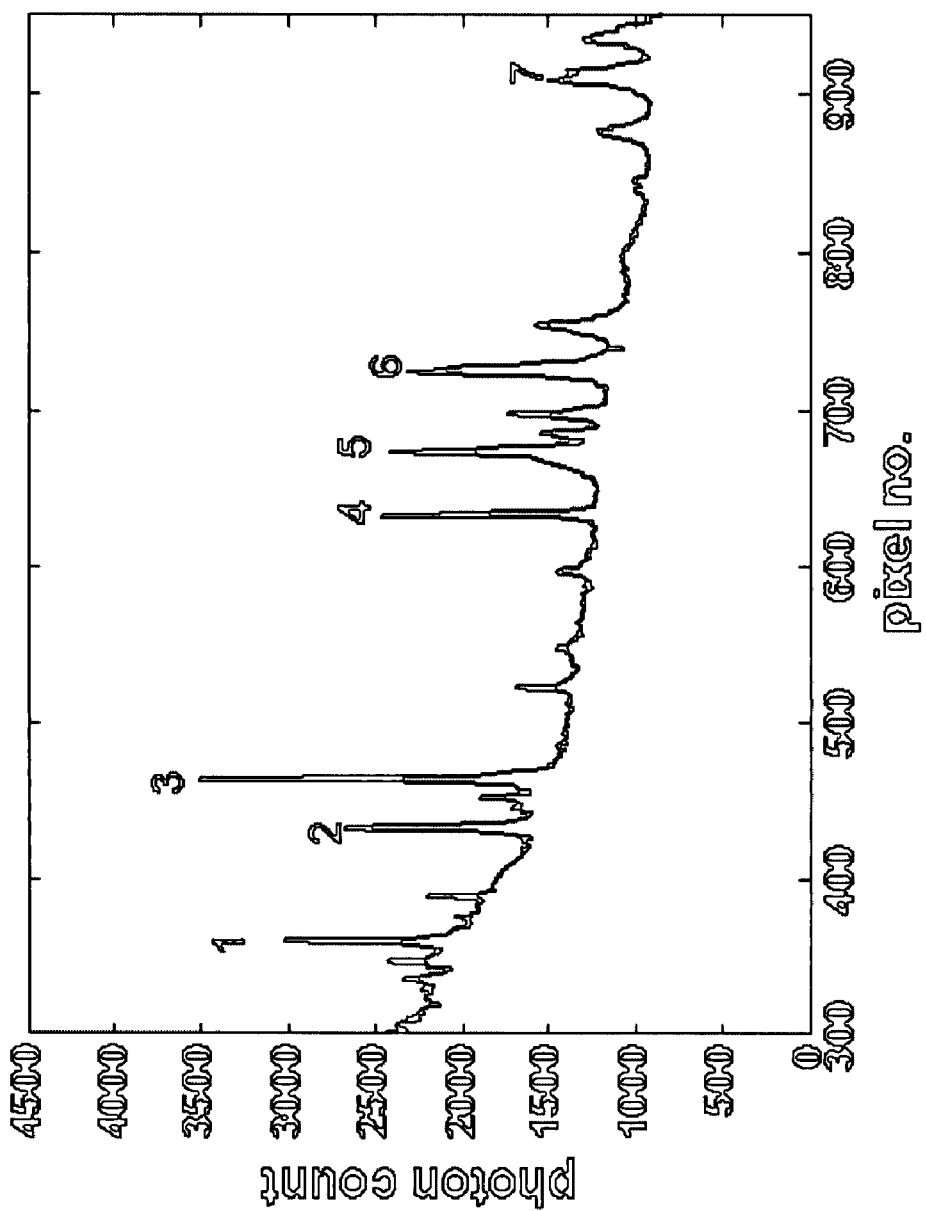
FIG. 13 shows the Raman spectrum standard of acetaminophen tablet. Major peaks are numerically identified for correlation with FIG. 12B.

Finally, the Raman spectra acquired from the centered tablet was compared to the standard Raman spectra of an acetaminophen tablet taken with the same system in order to confirm the chemical composition of the structural anomaly in the OCT image, as shown in FIG. 13. The correlation of the peaks in the two spectra confirms the chemical composition of the tablet as acetaminophen.

Although the Raman spectra collected from this experimental setup exhibit were not optimal due to the use of a spectrograph that was not specifically tuned for the excitation laser in use, and excessive stray light, these experiments demonstrate the ability of the combined RS-OCT system to utilize the complimentary data sets to enhance the functionality of both techniques. The system could be optimized by correcting the spectrograph and inserting filtering optics to reduce the laser line intensity transmitted through the dichroic mirror D2.

Raman spectroscopy is capable of determining the specific biochemical information composition of a tissue, but yields no structural data. OCT, on the other hand, enables analysis of tissue structure, but lacks the ability to discern the nature of the scattering elements in its image. By combining Raman spectroscopy and OCT into a single system, it is demonstrated the ability of the two modalities to compliment each other. Raman spectroscopy enables the chemical content of ambiguous structural in homogeneities in OCT to be discerned, while OCT can serve as a technique to guide placement of the Raman probe beam.

The combination of these two optical modalities into a single system allows for simultaneous structural and biochemical analysis of tissues and present a significant development towards the ultimate goal of "optical biopsy"; the entirely non-invasive diagnosis of potentially pathological tissues with optical techniques. Such a system would enable a significant cost-savings by reducing patient visits and facilitating the diagnostic and therapeutic procedures to be performed in a single visit. Additionally, such a system would allow for the thorough screening of patients with a large number of suspicious lesions and potentially even reduce the likelihood of undiagnosed disease. Two complimentary emerging optical modalities have recently emerged as promising diagnostic techniques for the skin; Raman spectroscopy and optical coherence tomography.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. Cancer Reference Information: Skin Cancer, American Cancer Society. 2006.

[2]. Moy, R. L. D. P. Taheri, and A. Ostad, *Practical Management of Skin Cancer.* 1999, Philadelphia: Lippincott-Raven Publishers.

[3]. Mehregan, A., et al., *Pinkus' Guide to Dermatohistopathology.* 6th ed. 1995, East Norwalk, Conn.: Appleton & Lange.

[4]. Haka, A. S., et al., In vivo margin assessment during partial mastectomy breast surgery using raman spectroscopy. Cancer Res, 2006. 66(6): p. 3317-22.

[5]. Haka, A. S., et al., Identifying microcalcifications in benign and malignant breast lesions by probing differences in their chemical composition using Raman spectroscopy. Cancer Res, 2002. 62(18): p. 5375-80.

[6]. Frank, C. J., R. L. McCreery, and D. C. Redd, Raman spectroscopy of normal and diseased human breast tissues. Anal Chem, 1995. 67(5): p. 777-83.

[7]. Stone, N., et al., Raman spectroscopy for identification of epithelial cancers. Faraday Discuss, 2004. 126: p. 141-57; discussion 169-83.

[8]. Mahadevan-Jansen, A., et al., Development of a fiber optic probe to measure NIR Raman spectra of cervical tissue in vivo. Photochem Photobiol, 1998. 68(3): p. 427-31.

[9]. Mahadevan-Jansen, A., et al., Near-infrared Raman spectroscopy for in vitro detection of cervical precancers. Photochem Photobiol, 1998. 68(1): p. 123-32.

[10]. Crow, P., et al., Assessment of fiberoptic near-infrared raman spectroscopy for diagnosis of bladder and prostate cancer. Urology, 2005. 65(6): p. 1126-30.

[11]. Huang, Z., et al., Near-infrared Raman spectroscopy for optical diagnosis of lung cancer. Int J Cancer, 2003. 107(6): p. 1047-52.

[12]. Molckovsky, A., et al., Diagnostic potential of near-infrared Raman spectroscopy in the colon: differentiating adenomatous from hyperplastic polyps. Gastrointest Endosc, 2003. 57(3): p. 396-402.

[13]. Huang, D., et al., Optical Coherence Tomography. Science, 1991. 254(5035): p. 1178-1181.

[14]. Izatt, J. A., et al., In vivo bidirectional color Doppler flow imaging of picoliter blood volumes using optical coherence tomograghy. Optics Letters, 1997. 22(18): p0. 1439-1441.

[15]. deBoer, J. F., et al., Two-dimensional birefringence imaging in biological tissue by polarization-sensitive optical coherence tomography. Optics Letters, 1997. 22(12): p. 934-936.

[16]. Morgner, U., et al., Spectroscopic optical coherence tomography. Optics Letters, 2000. 25(2): p. 111-113.

[17]. Faber, D. J., et al., Light absorption of (oxy-)hemoglobin assessed by spectroscopic optical coherence tomography. Opt Lett, 2003. 28(16): p. 1436-8.

[18]. Thomas, D. and G. Duguid, Optical coherence tomography—a review of the principles and contemporary uses in retinal investigation. Eye, 2004. 18(6): p. 561-70.

[19]. Hee, M. R., et al., Optical Coherence Tomography of the Human Retina. Archives of Opthalmology, 1995. 113(3): p. 325-332.

[20]. Chalita, M. R., et al., High-speed optical coherence tomography of laser iridotomy. Am J Opthalmol, 2005. 140(6): p. 1133-6.

[21]. Puliafito, C. A., et al., Imaging of Macular Diseases with Optical Coherence Tomography. Opthalmology, 1995. 102 (2): p. 217-229.

[22]. Swanson, E. A., et al., In-Vivo Retinal Imaging by Optical Coherence Tomography. Optics Letters, 1993. 18(21): p. 1864-1866.

[23]. Sivak, M. V., Jr., et al., High-resolution endoscopic imaging of the GI tract using optical coherence tomography. Gastrointest Endosc, 2000. 51(4 Pt 1): p. 474-9.

[24]. Jang, I. K., G. Tearney, and B. Bouma, Visualization of tissue prolapse between coronary stent struts by optical coherence tomography: comparison with intravascular ultrasound. Circulation, 2001. 104(22): p. 2754.

[25]. Welzel, J., Optical coherence tomography in dermatology: a review. Skin Res Technol, 2001. 7(1): p. 1-9.

[26]. Welzel, J., et al., Optical coherence tomography of the skin. Curr Probl Dermatol, 1998. 26: p. 27-37.

[27]. Vargas, G., et al., Use of an agent to reduce scattering in skin. Lasers Surg Med, 1999. 24(2): p. 133-41.

[28]. Welzel, J., M. Bruhns, and H. H. Wolff, Optical coherence tomography in contact dermatitis and psoriasis. Arch Dermatol Res, 2003. 295(2): p. 50-5.

[29]. Welzel, J., et al., Changes in function and morphology of normal human skin: evaluation using optical coherence tomography. Br J Dermatol, 2004. 150(2): p. 220-5.

[30]. Park, B. H., et al., In vivo burn depth determination by high-speed fiber-based polarization sensitive optical coherence tomography. J Biomed Opt, 2001. 6(4): p. 474-9.

[31]. Pierce, M. C., et al., Collagen denaturation can be quantified in burned human skin using polarization-sensitive optical coherence tomography. Burns, 2004. 30(6): p. 511-7.

[32]. Srinivas, S. M., et al., Determination of burn depth by polarization-sensitive optical coherence tomography. J Biomed Opt, 2004. 9(1): p. 207-12.

[33]. Bechara, F. G., et al., Histomorphologic correlation with routine histology and optical coherence tomography. Skin Res Technol, 2004. 10(3): p. 169-73.

[34]. de Giorgi, V., et al., Possible histopathologic correlates of dermoscopic features in pigmented melanocytic lesions identified by means of optical coherence tomography. Exp Dermatol, 2005. 14(1): p. 56-9.

[35]. Lieber, C. A., Detection of Skin Abnormalities using Confocal Raman Spectroscopy, in *Biomedical Engineering.* 2004, Vanderbilt University: Nashville, Tenn.

[36]. Rollins, A. M., et al., In vivo video rate optical coherence tomography. Optics Express, 1998. 3(6): p. 219-229.

[37]. Lieber, C. A. and A. Mahadevan-Jansen, Automated method for subtraction of fluorescence from biological Raman spectra. Applied Spectroscopy, 2003. 57(11): p. 1363-1367.

[38]. Mahadevan-Jansen, A. and R. Richards-Kortum, Raman Spectrscopy for the Detection of Cancers and Precancers. Journal of Biomedical Optics, 1996. 1(1): p. 31-70.

What is claimed is:

1. An apparatus that uses Raman spectroscopy and optical coherence tomography for non-invasively evaluating a target of interest of a living subject, comprising:
   a. a first light source for generating a broadband light characterized with a center wavelength, $\lambda 1$, and a spectral bandwidth, $\Delta$;
   b. a second light source for generating a monochromatic light at a single wavelength, $\lambda 2$;
   c. a beamsplitter optically coupled to the first light source for receiving the broadband light and splitting the received broadband light into a reference light and a sample light;
   d. a reference arm optically coupled to the beamsplitter for receiving the reference light and returning the received reference light into the beamsplitter;
   e. a probe having a working end placed proximal to a target of interest of a living subject, optically coupled to the beamsplitter and the second light source for receiving the sample light and the monochromatic light, delivering them from the working end onto the target of interest, collecting from the working end a backscattering light and a Raman scattering light that are obtained from interaction of the sample light and the monochromatic light with the target of interest, respectively, and returning the backscattering light into the beamsplitter so as to generate an interference signal between the returned backscattering light and the returned reference light in the beamsplitter, wherein the probe, the beamsplitter and the second light source are arranged such that the monochromatic light generated by the second light source is delivered into the probe without passing through the beamsplitter;
   f. a first detecting device optically coupled to the beamsplitter for collecting the interference signal to provide an interference pattern of the returned backscattering light and the returned reference light; and
   g. a second detecting device optically coupled to the probe for collecting the Raman scattering light to provide a frequency spectrum of the returned Raman scattering light, wherein the second detecting device and the probe are arranged such that the Raman scattering light returned from the probe is directly collected by the second detecting device without passing through the beamsplitter.

2. The apparatus of claim 1, further comprising an optical circulator having three ports optically coupled to the first light source, the beamsplitter and the first detecting device, respectively, wherein the optical circulator is configured such that when an optical signal is fed into and received by one of the three ports, the fed optical signal is transferred from the receiving port to a predetermined one of the other two ports port.

3. The apparatus of claim 1, further comprising a wavelength division multiplexer (WDM) optically coupled to the beamsplitter, the second light source and the probe for receiving the sample light and the monochromatic light from the beamsplitter and the second light source, respectively, and delivering the received sample and monochromatic light to the probe, and receiving the backscattering light from the probe and returning the received backscattering light into the beamsplitter.

4. The apparatus of claim 2, wherein the interference pattern contains information of morphological details of the target of interest, and wherein the frequency spectrum contains information of biochemical contents of the target of interest.

5. The apparatus of claim 4, wherein the interference pattern of the interference signal is associated with an optical coherence tomographic (OCT) image.

6. The apparatus of claim 5, wherein the spectral profile of the frequency spectrum of the Raman scattering light includes a plurality of intensity peaks at a plurality of wavelengths, each intensity peak associating with a specific biochemical content of the target of interest.

7. The apparatus of claim 6, further comprising a controller in communication with the first and second detecting devices and programmed to correlate the OCT image with the Raman scattering spectrum and determine the structures and biochemical content of the target of interest from the correlated OCT image and Raman scattering spectrum.

8. The apparatus of claim 7, wherein the controller is a computer having a display for displaying the OCT image and the Raman scattering spectrum.

9. The apparatus of claim 7, wherein the first detecting device comprises an OCT detector optically coupled to the beamsplitter and the optical circulator for receiving the OCT signal, a BP filter in communication with the OCT detector and a data acquisition (DAQ) member in communication with the BP filter and the controller.

10. The apparatus of claim 7, wherein the second detecting device comprises a spectrograph optically coupled to the probe for receiving the Raman scattering light, a charge-coupled detecting (CCD) camera in communication with the spectrograph and a DAQ member in communication with the CCD camera and the controller.

11. The apparatus of claim 1, wherein the reference arm is arranged such that the length of an optical path of the reference light propagating from the beamsplitter through the reference arm and back the beamsplitter is adjustable.

12. The apparatus of claim 11, wherein the reference arm comprises a mirror movable along the optical path of the reference light so as to adjust the optical path length.

13. The apparatus of claim 11, wherein the reference arm comprises a rapid scanning optical delay (RSOD) for adjusting the optical path length.

14. The apparatus of claim 13, wherein the RSOD comprises a fiber optical collimator, a grating, a phase control delay lens and a galvanometric mirror respectively placed along the optical path in such a configuration that in operation, the reference light is received by the fiber optical collimator and collimated onto the grating, and redirected by the grating to the galvanometric mirror through the phase control delay lens, which scans the reference light back towards the fiber optical collimator through the phase control delay lens and the grating, thereby adjusting the optical path length of the reference light propagating through the reference arm.

15. The apparatus of claim 1, wherein the probe having a casing having a first end and an opposite, second end, comprises:
   a. a first, a second and a third optical ports, wherein the first and second optical ports are located at the first end of the casing and the third optical port is located at the second end of the casing such that the first and third optical ports define a first optical path therebetween and the second and third optical ports define a second optical path therebetween, respectively, wherein each of the first and second optical paths has a first portion and a second portion, and wherein the second portions of the first and second optical paths are substantially overlapped and proximal to the third optical port;
   b. a collimation lens (C1), a coupling lens (C2), and an objective lens (OL);
   c. a first, a second and a third mirrors (M1, D, M2);

d. a dual-band pass filter (BP);

e. a notch filter (NF); and f. a scanning member (G), wherein the collimation lens (C1), the dual-band pass filter (BP), the first mirror (M1) are placed at the first portion of the first optical path, the coupling lens (C2) and the notch filter (NF) are placed at the first portion of the second optical path, and the second and third mirrors (D, M2), the scanning member (G) and the objective lens are placed at the overlapped second portion of the first and second optical paths, such that in operation, the sample light and the monochromatic light are received from the first port and collimated by the collimation lens (C1), passed through the dual-band pass filter (BP) and reflected to the galvanometer (G) by the first, second and third mirrors (M1, D, M2), which telecentrically scans them through the objective lens (OL) and the third optical port onto the target of interest, which, in response to illumination by the sample light and the monochromatic light, backscatters the sample light and the monochromatic light in the forms of backscattering light and Raman scattering light, respectively, which are collected through the third optical port by the objective lens, and reflected by the scanning member (G) and the third mirror (M2) to the second mirror (D), from which the backscattering light is reflected by the second mirror (D) and the first mirror (M1) to the dual-band pass filter (BP), and passed through the dual-band pass filter (BP) and the collimation lens to the first optical port, while the Raman scattering light is transmitted through the second mirror (D) to the notch filter (NF) and the coupling lens (C2) to the second optical port.

16. The apparatus of claim 15, wherein the second mirror (D) is a custom dichroic mirror configured to selectively transmit the Raman scattering light and reflect away light that is not the Raman scattering light.

17. The apparatus of claim 15, wherein the scanning member (G) comprises at least one of micro-electronic mirrors (MEMS), micro-optoelectrical mirrors (MOEMS), galvanometer devices, rotation motors, translational motors, and any combinations of them.

18. The apparatus of claim 15, wherein the objective lens (OL) comprises an achromatic doublet objective lens or a fused silica objective lens.

19. The apparatus of claim 15, wherein the probe further comprises a first optical connector optically coupled between the first optical ports and a single-mode fiber (SMF), and a second optical connector optically coupled between the second optical port and a multi-mode fiber (MMF), respectively.

20. The apparatus of claim 19, wherein the probe further comprises a lens tube (LT) adjustably placed between the third port and a position where the target of interest is to be placed in operation.

21. The apparatus of claim 1, wherein the first light source comprises light emitting diodes (LEDs), femtosecond lasers or broadband optical amplifiers.

22. The apparatus of claim 21, wherein the center wavelength $\lambda 1$ is in the range of 1100-1500 nm, and wherein the spectral bandwidth $\Delta$ is in the range of 20-100 nm.

23. The apparatus of claim 1, wherein the second light source comprises a laser.

24. The apparatus of claim 23, wherein the single wavelength $\lambda 2$ is in the range of 600-1000 nm.

25. The apparatus of claim 1, wherein the target of interest comprises tissues of the living subject.

26. An apparatus for non-invasively evaluating a target of interest of a living subject, comprising:

a. a first light source for generating a broadband light;

a. a second light source for generating a monochromatic light;

b. a beamsplitter optically coupled to the first light source for receiving the broadband light and splitting it into a reference light and a sample light; and c. a sample arm optically coupled to the beamsplitter and the second light source for combining the sample light and the monochromatic light, delivering the combined sample and monochromatic light to the target of interest, collecting a backscattering light and a Raman scattering light that are obtained from interaction of the sample light and the monochromatic light with the target of interest, respectively, and directing the collected backscattering light and Raman scattering light in different optical paths, comprising:

(i). a first collimating lens (C1) optically coupled to the beamsplitter for receiving the sample light and collimating the received sample light into a first optical path;

(ii). a second collimating lens (C2) optically coupled to the second light source for receiving the monochromatic light and collimating the received monochromatic light into a second optical path, wherein the first collimating lens (C1) and the second collimating lens (C2) are substantially identical;

(iii). a first dichroic mirror (D1) optically coupled to the first collimating lens (C1) and the second collimating lens (C2) for receiving the collimated sample light from the first collimating lens (C1) and the collimated monochromatic light from the second collimating lens (C2) and transmitting the received sample light into a third optical path and reflecting the received monochromatic light into the third optical path, respectively, such that the transmitted sample light and the reflected monochromatic light are combined in the third optical path;

(iv). a second dichroic mirror (D2) optically coupled to the first dichroic mirror (D1) for receiving the combined sample and monochromatic light and reflecting it into a fourth optical path;

(v). a scanning member optically coupled to the second dichroic mirror (D2) for receiving the reflected sample and monochromatic light and telecentrically scanning the received sample and monochromatic light onto a target of interest along a fifth optical path; and (vi). an objective lens optically coupled to the scanning member, placed at the fifth optical path and configured to receive the sample and monochromatic light scanned by the scanning member and focus the scanned sample and monochromatic light onto the target of interest, wherein in response, the target of interest backscatters the sample light and the monochromatic light in the forms of a backscattering light and a Raman scattering light, respectively, which are collected and focused to the scanning member by the objective lens (OL), and directed by the scanning member along the fourth optical path to the second dichroic mirror (D2), from which the Raman scattering light is transmitted by the second dichroic mirror (D2) into a sixth optical path, while the backscattering light is reflected by the second dichroic mirror (D2) along the third optical to the first dichroic mirror (D1), and transmitted by the first dichroic mirror (D1) along the first optical path to the first collimating lens (C1).

27. The apparatus of claim 26, wherein the sample arm further comprises a dual-band pass filter (BP) placed at the second optical path between the second collimation lens (C2) and the first dichroic mirror (D1).

28. The apparatus of claim 27, wherein the dual-band pass filter (BP) is characterized with a central bandpass wavelength corresponding to a wavelength of the monochromatic light.

29. The apparatus of claim 26, wherein the sample arm further comprises a coupling lens (C3) optically coupled to the second dichroic mirror (D2) and placed at the sixth optical path for receiving the Raman scattering light transmitted from the second dichroic mirror (D2).

30. The apparatus of claim 29, wherein the sample arm further comprises a notch filter (NF) placed at the sixth optical path between the second dichroic mirror (D2) and the coupling lens (C3) for eliminating residual elastically scattering light at the single wavelength of the monochromatic light.

31. The apparatus of claim 26, wherein the beamsplitter comprises an OCT 2×2 fiber coupler.

32. The apparatus of claim 26, further comprising an optical coherence tomographic (OCT) signal detector optically coupled to the beamsplitter for detecting the interference signal to provide an interference pattern of the returned backscattering light and the returned reference light.

33. The apparatus of claim 26, further comprising a second detecting device optically coupled to the probe for detecting the Raman scattering light to provide a frequency spectrum of the returned Raman scattering light.

34. The apparatus of claim 26, wherein the scanning member comprises at least one of micro-electronic mirrors (MEMS), micro-optoelectrical mirrors (MOEMS), galvanometer devices, rotation motors, translational motors, and any combinations of them.

35. The apparatus of claim 26, wherein the dichroic mirror (D1) is configured to reflect the monochromatic light and transmit a light that is not the monochromatic light.

36. The apparatus of claim 26, wherein the dichroic mirror (D2) is configured to transmit the Raman scattering light and reflect a light that is not the Raman scattering light.

37. The apparatus of claim 26, wherein the objective lens (OL) comprises an achromatic doublet objective lens or a fused silica objective lens.

38. The apparatus of claim 26, wherein the reference light transmits from the beamsplitter through the reference arm and returns into the beamsplitter along a reference path having a length that is adjustable.

39. The apparatus of claim 26, wherein the sample light transmits from the beamsplitter through the sample arm to the target of interest, and is backscattered by the target of interest into the beamsplitter through the sample arm along a sample path having a length that is adjustable depending upon the structure of the target of interest to be examined.

40. The apparatus of claim 26, wherein the broadband light is characterized with a center wavelength, $\lambda 1$, and a spectral bandwidth, $\Delta$, and wherein the center wavelength $\lambda 2$ is in the range of 1100-1500 nm, and wherein the spectral bandwidth $\Delta$ is in the range of 20-100 nm.

41. The apparatus of claim 26, wherein the single wavelength $\lambda 2$ is in the range of 600-1000 nm.

42. The apparatus of claim 26, wherein the target of interest of a living subject comprises tissues of a living subject.

43. A method for non-invasively evaluating a target of interest of a living subject, comprising the steps of:
   a. generating a broadband light by a first light source and a monochromatic light by a second light source;
   b. splitting the broadband light by a beamsplitter into a reference light and a sample light;
   c. co-aligning the sample light and the monochromatic light into an optical path;
   d. scanning the co-aligned sample and monochromatic light onto a target of interest along the optical path to a probe,
   wherein the probe, the beamsplitter and the second light source are arranged such that the monochromatic light generated by the second light source is delivered into the probe without passing through the beamsplitter;
   e. collecting a backscattering light and a Raman scattering light that are obtained from interaction of the sample light and the monochromatic light with the target of interest, respectively;
   f. interfering the collected backscattering light with the reference light to provide an interference signal; and
   g. processing the interference signal collected by a first detecting device and the Raman scattering light collected by a second detecting device to provide morphological details and biochemical contents of the target of interest, respectively, wherein the second detecting device and the probe are arranged such that the Raman scattering light returned from the probe is directly collected by the second detecting device without passing through the beamsplitter.

44. The method of claim 43, wherein the broadband light is characterized with a center wavelength, $\mu 1$, and a spectral bandwidth, $\Delta$, and wherein $\lambda 1$ is in the range of 1100-1500 nm and $\Delta$ is in the range of 20-100 nm.

45. The method of claim 43, wherein the monochromatic light has a single wavelength, $\lambda 2$, and wherein $\lambda 2$ is in the range of 600-1000 nm.

46. The method of claim 43, wherein the interference signal is processed in the form of an optical coherence tomographic (OCT) image.

47. The method of claim 46, wherein the Raman scattering light is processed in the form of a frequency spectrum having a plurality of intensity peaks at a plurality of wavelengths, each intensity peak associating with a specific biochemical content of the target of interest.

48. The method of claim 47, wherein the processing step comprises the step of correlating the OCT image with the frequency spectrum.

49. The method of claim 43, wherein the target of interest of a living subject comprises tissues of a living subject.

50. A probe usable in a combined Raman spectroscopy and optical coherence tomography (RS-OCT) system, having a casing having a first end and an opposite, second end, comprising:
   a. a first, a second and a third optical ports, wherein the first and second optical ports are located at the first end of the casing and the third optical port is located at the second end of the casing such that the first and third optical ports define a first optical path therebetween and the second and third optical ports define a second optical path therebetween, respectively, wherein each of the first and second optical paths has a first portion and a second portion and wherein the second portions of the first and second optical paths are substantially overlapped and proximal to the third optical port;
   b. a collimation lens (C1), a coupling lens (C2), and an objective lens (OL);
   c. a first, a second and a third mirrors (M1, D, M2); and d. a scanning member (G) for scanning a beam of light onto a target of interest of a living subject, wherein the beam of light comprises a broadband light and a monochromatic light, wherein the collimation lens (C1), the first mirror (M1) are placed at the first portion of the first optical path, the coupling lens (C2) is placed at the first portion of the second optical path and proximal to the second optical port, and the second and third mirrors (D, M2), the galvanometer (G) and the objective lens are placed at the overlapped second portion of the first and second optical paths, such that in operation, the beam of light is received from the first port and collimated by the collimation lens (C1) onto the first mirror (M1), and redirected to the scanning member (G) by the first, second and third mirrors (M1, D, M2), which telecentrically scans the beam of light through the objective lens (OL) and the third optical port onto the target of interest, which, in response to illumination by the broadband light and the monochromatic light, backscatters the sample light and the monochromatic light in the forms of a backscattering light and a Raman scattering light, respectively, which are collected through the third optical port by the objective lens, and directed by the scanning member (G) and the third mirror (M2) to the second mirror (D), from which the backscattering light is reflected by the second mirror (D) and the first mirror (M1) onto the collimation lens and transmitted by the collimation lens to the first optical port, while the Raman scattering light is transmitted through the second mirror (D) and the coupling lens (C2) to the second optical port.

51. The probe of claim 50, further comprising a first optical connector optically coupled between the first optical port and a single-mode fiber (SMF), and a second optical connector optically coupled between the second optical port and a multi-mode fiber (MMF), respectively.

52. The probe of claim 50, further comprising a dual-band pass filter (BP) placed at the first portion of the first optical path between the collimation lens (C1) and the first mirror (M1), and adapted for filtering out fiber fluorescence.

53. The probe of claim 50, further comprising a notch filter (NF) placed at the first portion of the second optical path between the coupling lens (C2) and the second mirror (D), and configured to eliminate a residual elastically scattering light backscattered from the target of interest.

54. The probe of claim 50, wherein the scanning member (G) comprises at least one of micro-electronic mirrors (MEMS), micro-optoelectrical mirrors (MOEMS), galvanometer devices, rotation motors, translational motors, or any combinations of them.

55. The probe of claim 50, wherein the second mirror (D) is a custom dichroic mirror configured to transmit the Raman scattering light and reflect a light that is not the Raman scattering light.

56. The probe of claim 50, wherein the objective lens (OL) comprises an achromatic doublet objective lens or a fused silica objective lens.

57. The probe of claim 50, further comprising a lens tube (LT) adjustably placed between the third port and a position that the target of interest is to be placed in operation.

* * * * *

UNITED STATES PATENT AND TRADEMARK OFFICE
CERTIFICATE OF CORRECTION

| | | |
|---|---|---|
| PATENT NO. | : 7,508,524 B2 | Page 1 of 1 |
| APPLICATION NO. | : 11/780793 | |
| DATED | : March 24, 2009 | |
| INVENTOR(S) | : Anita Mahadevan-Jansen et al. | |

It is certified that error appears in the above-identified patent and that said Letters Patent is hereby corrected as shown below:

At column 1, line 5, before "Cross-Reference to Related Patent Application", insert:

--STATEMENT OF FEDERALLY-SPONSORED RESEARCH

This invention was made in part with U.S. Government support under Grant R21CA133477, awarded by the National Institute of Health. The U.S. Government has certain rights in this invention.--

Signed and Sealed this

Fourteenth Day of July, 2009

JOHN DOLL
*Acting Director of the United States Patent and Trademark Office*